United States Patent
Pan et al.

(10) Patent No.: US 8,383,890 B1
(45) Date of Patent: Feb. 26, 2013

(54) **GENES ENCODING FATTY ACID DESATURASES FROM *SORGHUM BICOLOR***

(75) Inventors: Zhiqiang Pan, Oxford, MS (US); Agnes M. Rimando, Oxford, MS (US); Scott R. Baerson, Oxford, MS (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 747 days.

(21) Appl. No.: 11/639,709

(22) Filed: Dec. 15, 2006

(51) Int. Cl.
*A01H 5/00* (2006.01)
*C12N 15/82* (2006.01)
*C07H 21/04* (2006.01)

(52) U.S. Cl. ........ 800/298; 800/281; 435/419; 536/23.2

(58) Field of Classification Search ........................ None
See application file for complete search history.

(56) References Cited

U.S. PATENT DOCUMENTS

2005/0132442 A1* 6/2005 Yadav et al. .................. 800/281

OTHER PUBLICATIONS

Yang et al, J Exp Bot 55 (406) 2251-2259, Oct. 2004.*
Sequence alignment of SEQ ID No. 3 with Accession AY566285 (Yang et al), run date Dec. 11, 2008.*
Sequence alignment of SEQ ID No. 4 with Accession AY566285 (Yang et al), run date Dec. 11, 2008.*
Sequence alignment of SEQ ID No. 11 with Accession AY566285 (Yang et al) run date Sep. 1, 2009.*

* cited by examiner

*Primary Examiner* — Elizabeth McElwain
(74) *Attorney, Agent, or Firm* — John D. Fado; Evelyn M. Rabin

(57) ABSTRACT

This invention relates to the fatty acid desaturase genes, designated SbDES2 and SbDES3, cloned from an expressed sequence tag (EST) database prepared from isolated root hairs from sorghum. Heterologous expression of the cDNAs in *S. cerevisiae* revealed that recombinant SbDES2 converted palmitoleic acid $(16:1\Delta^9)$ to hexadecadienoic acid $(16:2\Delta^{9, 12})$, and that recombinant SbDES3 was capable of converting hexadecadienoic acid into hexadecatrienoic acid $(16:3\Delta^{9, 12, 15})$. Desaturase enzymes capable of performing desaturation reactions producing a terminal double bond have not previously been characterized in a plant system.

30 Claims, 8 Drawing Sheets

Abbreviations: EV, empty vector control; bp, base pairs.

SEQUENCE LISTING

```
<160> NUMBER OF SEQ ID NOS: 20

<210> SEQ ID NO 1
<211> LENGTH: 1514
<212> TYPE: DNA
<213> ORGANISM: Sorghum bicolor

<400> SEQUENCE: 1
ggagcacacc accactcgtt ttcctgtccg gaacaggaga aaaggggagc gaggcgacta      60
ggcgaggcgc ggtgtccgcc cgatcagctc cgtcccgtcc cgacagcaaa atgggtgccg     120
gtggcaagat gactgagcag gagagggaga agcaggagca gcagctcgcc cgcggtgctt     180
caacaatgca gcgctcaccg gtggagaagc ctccgttcac ggtgggtcag atcaagaagg     240
ccatccctcc acactgcttc cagcgctcag tgttgaagtc cttctcctac gtggtccgtg     300
acctcgtcat tgccgcggcg ctcctgtact tcgcgctggc catcataccg gcgctcccaa     360
gcccgctgca ctacgccgcc tggccgctct actggatcgc ccaggggtgc gtgtgcttcg     420
ccatgtgggt catcgcgcac gagtgcggcc accacgcctt ctccgactac cagctcctgg     480
acgacatcgt gggcctggtg ctgcactcct cgctgatggt gccctacttc tcgtggaagt     540
acagccaccg ccgccaccac tccaacaccg gctccctgga gcgcgacgag gtgttcgtgc     600
caaagacgaa gggggcgctg gcgtggtacg ccccgtacgt gtacaacaac cccgtcgggc     660
ggctggtgca catcgtcgtg cagctcaccc tcgggtggcc gctgtacctg gccaccaacg     720
tgtcgggacg cccgtacccg cgcttcgcct gccactacga cccctacggc ccgatctaca     780
acgaccggga gcgcgcgcag atcttcgtct cggacgccgg cgtcatggcc gtctcgttcg     840
ggctgtacaa gctggcggcg accttggggt tctggtgggt ggtgcgcgtc tacgccgtgc     900
cgctgctgat cgtgaacgtg tggctggttc tcgtcacgta cctgcaccac acccacccgg     960
cgctccccca ctacgactcg agggagtggg actggctgcg cggcgcgctg tccaccgtgg    1020
accgcgacta cggcgtcttc aaccgttttt tccacaacat caccgacaca cacgtcgtgc    1080
accacctctt ctccacgctg ccgcacttcc acgccacgga ggctaccaag gcgatcaagc    1140
ccatcctcgg cgagtactac cagttcgacc ccactcccat cgccaaggcg acctggcgcg    1200
aagccaggga gtgcatcttt gtcgagcccg aggaaggcag gggcgtcttc tggtacaaca    1260
agttctagct gcttgatgcg cggaactcag gattgaggtg atcgtccata ctttcaccgg    1320
attgggagaa gaaatcagga agagaaggcg gtaaaaatgt tgtaccgagt gtccatccac    1380
cgatacatgg ttatagtcat cactcttcaa tctttttttt tcaaaaggcg gcaacaaact    1440
tttgccggat ttttatttga taaggaaaac gaaaataaat ggatttacag tcttacaaaa    1500
aaaaaaaaaa aaaa                                                     1514

<210> SEQ ID NO 2
<211> LENGTH: 385
<212> TYPE: PRT
<213> ORGANISM: Sorghum bicolor
```

```
<400> SEQUENCE: 2

Met Gly Ala Gly Gly Lys Met Thr Glu Gln Glu Arg Glu Lys Gln Glu
1               5                   10                  15

Gln Gln Leu Ala Arg Gly Ala Ser Thr Met Gln Arg Ser Pro Val Glu
            20                  25                  30

Lys Pro Pro Phe Thr Val Gly Gln Ile Lys Lys Ala Ile Pro Pro His
            35                  40                  45

Cys Phe Gln Arg Ser Val Leu Lys Ser Phe Ser Tyr Val Val Arg Asp
50                  55                  60

Leu Val Ile Ala Ala Leu Leu Tyr Phe Ala Leu Ala Ile Ile Pro
65                  70                  75                  80

Ala Leu Pro Ser Pro Leu His Tyr Ala Ala Trp Pro Leu Tyr Trp Ile
                85                  90                  95

Ala Gln Gly Cys Val Cys Phe Ala Met Trp Val Ile Ala His Glu Cys
                100                 105                 110

Gly His His Ala Phe Ser Asp Tyr Gln Leu Leu Asp Asp Ile Val Gly
            115                 120                 125

Leu Val Leu His Ser Ser Leu Met Val Pro Tyr Phe Ser Trp Lys Tyr
130                 135                 140

Ser His Arg Arg His Ser Asn Thr Gly Ser Leu Glu Arg Asp Glu
145                 150                 155                 160

Val Phe Val Pro Lys Thr Lys Gly Ala Leu Ala Trp Tyr Ala Pro Tyr
                165                 170                 175

Val Tyr Asn Asn Pro Val Gly Arg Leu Val His Ile Val Gln Leu
                180                 185                 190

Thr Leu Gly Trp Pro Leu Tyr Leu Ala Thr Asn Val Ser Gly Arg Pro
            195                 200                 205

Tyr Pro Arg Phe Ala Cys His Tyr Asp Pro Tyr Gly Pro Ile Tyr Asn
210                 215                 220

Asp Arg Glu Arg Ala Gln Ile Phe Val Ser Asp Ala Gly Val Met Ala
225                 230                 235                 240

Val Ser Phe Gly Leu Tyr Lys Leu Ala Ala Thr Leu Gly Phe Trp Trp
                245                 250                 255

Val Val Arg Val Tyr Ala Val Pro Leu Leu Ile Val Asn Val Trp Leu
                260                 265                 270

Val Leu Val Thr Tyr Leu His His Thr His Pro Ala Leu Pro His Tyr
            275                 280                 285

Asp Ser Arg Glu Trp Asp Trp Leu Arg Gly Ala Leu Ser Thr Val Asp
            290                 295                 300

Arg Asp Tyr Gly Val Phe Asn Arg Phe Phe His Asn Ile Thr Asp Thr
305                 310                 315                 320

His Val Val His His Leu Phe Ser Thr Leu Pro His Phe His Ala Thr
                325                 330                 335

Glu Ala Thr Lys Ala Ile Lys Pro Ile Leu Gly Glu Tyr Tyr Gln Phe
            340                 345                 350

Asp Pro Thr Pro Ile Ala Lys Ala Thr Trp Arg Glu Ala Arg Glu Cys
            355                 360                 365

Ile Phe Val Glu Pro Glu Glu Gly Arg Gly Val Phe Trp Tyr Asn Lys
    370                 375                 380

Phe
385

<210> SEQ ID NO 3
```

```
<211> LENGTH: 1538
<212> TYPE: DNA
<213> ORGANISM: Sorghum bicolor

<400> SEQUENCE: 3
ggacgacgcc gccaccaccg caaaagcagc aaaaccttag cttgttcacc accacaaccg     60
ccagccatgg cggcgacgga tcatgaggtt gaggaggcgg tggcgaaggc gagagaggac    120
gacaagagcc ggcggcaggt ggacggcttc gacgctggga aggcgccgcc gttccgcatt    180
ggcgacgtgc gggcggcggt gccggagcac tgctggcgca agagccctg gcggtcgctg     240 tggtacgtgg tgcgggacgt ggcggtggtg gtggcgctgg gagcggcggc ggcggccatg    300
gatagctggg cggtgtggcc gctctactgg gcggtgcagg ggaccatgtt ctgggcgttc    360
ttcgtcttgg acacgactg tggtcatggg agcttctcgg acaacgcgac gcttaacagc    420
gtggttggtc atctcctcca ctccttcatc ctcatcccct accatggatg gaggatcagc    480
cacagaacac atcatcagaa ccacggccac gtcgacaggg acgagtcatg gcacccgctg    540
acggagcggc ggtaccggcg attgcctcct cgcgcaaaga agctaagatt cacgcccccc    600
ttcccgctgc tcttattccc cctctacctg ttctacagga gccctggcaa gagggggctct   660 cactttcttc ccagcagccc actgttcagc cccaaggaca agggcgacgt catactctcg    720
accacctgct ggtgcatcat gctcgccttc ctcctcgcca tgtcgtgcgc gttcggccca    780
ctccaggtgc tcaagatgta cggcgttcca tacctggtgt ctgtgatgtg gcttgacttg    840
gtgacttacc tgcaccacca tgggcaccag gagcgcctcc cctggtaccg cggcgaggaa    900
tggagctacc tcccgcggcgg gctgacgacg gtggacagag actacggctg gatcaacagc    960
atccaccacg acatcggcac ccatgtcatc caccacctct ccccgcagat cccgcactac   1020
catctcgtcg aagctaccaa ggcagccaag ccggtgctgg ggcgatacta ccgggagcca   1080
cacaagtcag ggccgctgcc acttcacctc cttggcgtgc tcctcaggag cctcagagtc   1140
gaccacttcg tcagcgacca tggcgatgtt gtctactacc aaactgacca tcacctcaac   1200
gacactacta ctgatgatgc tcataagcaa aaatgacttg catcattgct gggagggatc   1260
cattccatgc ctgcgctttg ccagctggga ataatgatag atgcccgtac gtacgtctcg   1320
atatgcatac ggttgatgtt ggtgttgaat acctcgcgct ctcgtattcg tatcggagt    1380 agtaggtgaa gtcagttggt gcaatgtatt ccatctgttc gtggcctata tattatgcaa   1440
aaaaataatg tcagaataat taaatcacat gtgtgagatt gaataaataa ccaatttctc   1500
cgcatcgttt gtaaaaaaaa aaaaaaaaaa aaaaaaaa                           1538

<210> SEQ ID NO 4
<211> LENGTH: 389
<212> TYPE: PRT
<213> ORGANISM: Sorghum bicolor

<400> SEQUENCE: 4

Met Ala Ala Thr Asp His Glu Val Glu Glu Ala Val Ala Lys Ala Arg
1               5                   10                  15

Glu Asp Asp Lys Ser Arg Arg Gln Val Asp Gly Phe Asp Ala Gly Lys
            20                  25                  30

Ala Pro Pro Phe Arg Ile Gly Asp Val Arg Ala Ala Val Pro Glu His
        35                  40                  45

Cys Trp Arg Lys Ser Pro Trp Arg Ser Leu Trp Tyr Val Val Arg Asp
    50                  55                  60

Val Ala Val Val Val Ala Leu Gly Ala Ala Ala Ala Ala Met Asp Ser
65                  70                  75                  80
```

```
Trp Ala Val Trp Pro Leu Tyr Trp Ala Val Gln Gly Thr Met Phe Trp
                 85                  90                  95

Ala Phe Phe Val Leu Gly His Asp Cys Gly His Gly Ser Phe Ser Asp
            100                 105                 110

Asn Ala Thr Leu Asn Ser Val Val Gly His Leu Leu His Ser Phe Ile
        115                 120                 125

Leu Ile Pro Tyr His Gly Trp Arg Ile Ser His Arg Thr His His Gln
    130                 135                 140

Asn His Gly His Val Asp Arg Asp Glu Ser Trp His Pro Leu Thr Glu
145                 150                 155                 160

Arg Arg Tyr Arg Arg Leu Pro Pro Arg Ala Lys Lys Leu Arg Phe Thr
                165                 170                 175

Pro Pro Phe Pro Leu Leu Leu Phe Pro Leu Tyr Leu Phe Tyr Arg Ser
            180                 185                 190

Pro Gly Lys Arg Gly Ser His Phe Leu Pro Ser Ser Pro Leu Phe Ser
        195                 200                 205

Pro Lys Asp Lys Gly Asp Val Ile Leu Ser Thr Thr Cys Trp Cys Ile
    210                 215                 220

Met Leu Ala Phe Leu Leu Ala Met Ser Cys Ala Phe Gly Pro Leu Gln
225                 230                 235                 240

Val Leu Lys Met Tyr Gly Val Pro Tyr Leu Val Ser Val Met Trp Leu
                245                 250                 255

Asp Leu Val Thr Tyr Leu His His Gly His Gln Glu Arg Leu Pro
            260                 265                 270

Trp Tyr Arg Gly Glu Glu Trp Ser Tyr Leu Arg Gly Gly Leu Thr Thr
        275                 280                 285

Val Asp Arg Asp Tyr Gly Trp Ile Asn Ser Ile His His Asp Ile Gly
    290                 295                 300

Thr His Val Ile His His Leu Phe Pro Gln Ile Pro His Tyr His Leu
305                 310                 315                 320

Val Glu Ala Thr Lys Ala Ala Lys Pro Val Leu Gly Arg Tyr Tyr Arg
                325                 330                 335

Glu Pro His Lys Ser Gly Pro Leu Pro Leu His Leu Leu Gly Val Leu
            340                 345                 350

Leu Arg Ser Leu Arg Val Asp His Phe Val Ser Asp His Gly Asp Val
        355                 360                 365

Val Tyr Tyr Gln Thr Asp His His Leu Asn Asp Thr Thr Thr Asp Asp
    370                 375                 380

Ala His Lys Gln Lys
385

<210> SEQ ID NO 5
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 5
ccaaggaggt gaagtggcag                                                 20

<210> SEQ ID NO 6
<211> LENGTH: 22
<212> TYPE: DNA
<213> ORGANISM: Artificial Sequence
<220> FEATURE:
<223> OTHER INFORMATION: Chemically Synthesized
```

```
<400> SEQUENCE: 6
atactaccgg gagccacaca ag                                              22

<210> SEQ ID NO 7
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 7
tcgctgacga aatggttgac                                                 20

<210> SEQ ID NO 8
<211> LENGTH: 19
<212> TYPE: DNA
<213> ORGANISM: Artificial Sequence
<220> FEATURE:
<223> OTHER INFORMATION: Chemically Synthesized

<400> SEQUENCE: 8
cctccttggc gtgttcctc                                                  19

<210> SEQ ID NO 9
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 9
tggacgatca cctcaatcct g                                               21

<210> SEQ ID NO 10
<211> LENGTH: 24
<212> TYPE: DNA
<213> ORGANISM: Artificial Sequence
<220> FEATURE:
<223> OTHER INFORMATION: Chemically Synthesized

<400> SEQUENCE: 10
caacaagttc tagctgcttg atgc                                            24

<210> SEQ ID NO 11
<211> LENGTH: 1272
<212> TYPE: DNA
<213> ORGANISM: Sorghum bicolor

<400> SEQUENCE: 11
gagacccaaa aagcagcgac cttttgttca ccacaaccgc gcgccaccat ggcgacgacg      60
ccgatgacgg tggtggatca tgaggctgag gaggcggtgg cgaaggcgag agaggacgac     120
aagagccggc aggtggacgc cttcgacgcc gggaagccgc cgccgttccg cattggcgac     180
gtgcgcgcgg cggtgccgga gcactgctgg cacaagagcc cctggcggtc gctgtggtac     240
gtggtacggg acgtggcggc ggtggtgcg ctggaacgg cggcggcggc catggatagc       300
tgggcggtgt ggcccgtgta ctgggcggtg caagggacca tgttctgggc gttcttcgtc     360
ttgggacatg actgtggtca cgggagcttc tcggacagcc ggacgctcaa cagcgtggtt     420
ggtcatctcc tccactcctt tatcctcatc ccctaccatg gatggaggat cagccacaga     480
acacaccatc agaaccacgg gcacgtcgac agggacgaat catggcaccc gatcacggag     540
gggcggtacc ggcgattgcc tcctcgcgca aagaagataa gattcacggc ccctacccg      600
```

```
ctcctcttat tccccctcta cctgttctac cggggccccg acaagccagg cactcacttt    660
cttcccagca gcgagctgtt cagccccaag gagaagggcg acgtcatgct gtcaaccacc    720
tgctggtgca tcatgctcgc ctccctcctc gccatgtcgt gcgcattcgg cccactccag    780
gtcctcaaga tgtacggcct tccatacctg gtgtttgtga tgtggcttga cttggtgacg    840
tacctgcacc accatgggca ccatgagcgc ctccccggt accgcggcga ggagtggagc     900
tacctgcgcg gcgggctgac gacggtggac agggactacg gctggatcaa caagatccac    960
cacgacatcg gcacccatgt catccaccac ctcttcccac agatcccgca ctaccatctc   1020
gtcgaagcta ccaaggcagc caagccggtg ttggggcgat actaccggga gccacagaag   1080
tcagggccgc tgccacttcc cctccttggc gtgttcctca ggagcatcag agtcaaccat   1140
ttcgtcagcg accatgggga tgttgtctac taccaaactg accatcacct caacgacact   1200
actaagcaaa aatgacttga tgcattggga gcgagggatc cattccatgc acccttcgc    1260 tgcgcttgcc at                                                      1272
```

<210> SEQ ID NO 12
<211> LENGTH: 388
<212> TYPE: PRT
<213> ORGANISM: Sorghum bicolor

<400> SEQUENCE: 12

```
Met Ala Thr Thr Pro Met Thr Val Val Asp His Glu Ala Glu Ala
1               5                   10                  15

Val Ala Lys Ala Arg Glu Asp Asp Lys Ser Arg Gln Val Asp Ala Phe
            20                  25                  30

Asp Ala Gly Lys Pro Pro Phe Arg Ile Gly Asp Val Arg Ala Ala
        35                  40                  45

Val Pro Glu His Cys Trp His Lys Ser Pro Trp Arg Ser Leu Trp Tyr
    50                  55                  60

Val Val Arg Asp Val Ala Ala Val Val Ala Leu Gly Thr Ala Ala Ala
65                  70                  75                  80

Ala Met Asp Ser Trp Ala Val Trp Pro Val Tyr Trp Ala Val Gln Gly
                85                  90                  95

Thr Met Phe Trp Ala Phe Phe Val Leu Gly His Asp Cys Gly His Gly
            100                 105                 110

Ser Phe Ser Asp Ser Arg Thr Leu Asn Ser Val Val Gly His Leu Leu
        115                 120                 125

His Ser Phe Ile Leu Ile Pro Tyr His Gly Trp Arg Ile Ser His Arg
    130                 135                 140

Thr His His Gln Asn His Gly His Val Asp Arg Asp Glu Ser Trp His
145                 150                 155                 160

Pro Ile Thr Glu Gly Arg Tyr Arg Arg Leu Pro Pro Arg Ala Lys Lys
                165                 170                 175

Ile Arg Phe Thr Ala Pro Tyr Pro Leu Leu Phe Pro Leu Tyr Leu
            180                 185                 190

Phe Tyr Arg Gly Pro Asp Lys Pro Gly Thr His Phe Leu Pro Ser Ser
        195                 200                 205

Glu Leu Phe Ser Pro Lys Glu Lys Gly Asp Val Met Leu Ser Thr Thr
    210                 215                 220

Cys Trp Cys Ile Met Leu Ala Ser Leu Leu Ala Met Ser Cys Ala Phe
225                 230                 235                 240

Gly Pro Leu Gln Val Leu Lys Met Tyr Gly Leu Pro Tyr Leu Val Phe
                245                 250                 255
```

```
Val Met Trp Leu Asp Leu Val Thr Tyr Leu His His His Gly His His
            260                 265                 270

Glu Arg Leu Pro Trp Tyr Arg Gly Glu Trp Ser Tyr Leu Arg Gly
        275                 280                 285

Gly Leu Thr Thr Val Asp Arg Asp Tyr Gly Trp Ile Asn Lys Ile His
    290                 295                 300

His Asp Ile Gly Thr His Val Ile His His Leu Phe Pro Gln Ile Pro
305                 310                 315                 320

His Tyr His Leu Val Glu Ala Thr Lys Ala Ala Lys Pro Val Leu Gly
            325                 330                 335

Arg Tyr Tyr Arg Glu Pro Gln Lys Ser Gly Pro Leu Pro Leu Pro Leu
        340                 345                 350

Leu Gly Val Phe Leu Arg Ser Ile Arg Val Asn His Phe Val Ser Asp
    355                 360                 365

His Gly Asp Val Val Tyr Tyr Gln Thr Asp His His Leu Asn Asp Thr
    370                 375                 380

Thr Lys Gln Lys
385

<210> SEQ ID NO 13
<211> LENGTH: 29
<212> TYPE: DNA
<213> ORGANISM: Artificial Sequence
<220> FEATURE:
<223> OTHER INFORMATION: Chemically Synthesized

<400> SEQUENCE: 13
gggcgcgcca cggattagaa gccgccgag                                         29

<210> SEQ ID NO 14
<211> LENGTH: 27
<212> TYPE: DNA
<213> ORGANISM: Artificial Sequence
<220> FEATURE:
<223> OTHER INFORMATION: Chemically Synthesized

<400> SEQUENCE: 14
gggcgcgccg caaattaaag ccttcga                                           27

<210> SEQ ID NO 15
<211> LENGTH: 26
<212> TYPE: DNA
<213> ORGANISM: Artificial Sequence
<220> FEATURE:
<223> OTHER INFORMATION: Chemically Synthesized

<400> SEQUENCE: 15
acaacatttt taccgccttc tcttcc                                            26

<210> SEQ ID NO 16
<211> LENGTH: 26
<212> TYPE: DNA
<213> ORGANISM: Artificial Sequence
<220> FEATURE:
<223> OTHER INFORMATION: Chemically Synthesized

<400> SEQUENCE: 16
aacacgagag cgcgaggtat tcaaca                                            26

<210> SEQ ID NO 17
<211> LENGTH: 20
<212> TYPE: DNA
```

```
<213> ORGANISM: Artificial Sequence
<220> FEATURE:
<223> OTHER INFORMATION: Chemically Synthesized

<400> SEQUENCE: 17
gcctgccact acgacccta                                                   20

<210> SEQ ID NO 18
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 18
agatgcactc cctggcttcg                                                  20

<210> SEQ ID NO 19
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 19
ccccttcccg ctgctcttat                                                  20

<210> SEQ ID NO 20
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 20
agcacgccaa ggaggtgaag                                                  20
```

US 8,383,890 B1

GENES ENCODING FATTY ACID DESATURASES FROM *SORGHUM BICOLOR*

BACKGROUND OF THE INVENTION

1. Field of the Invention

This invention relates to two fatty acid desaturase genes cloned from sorghum, the sorghum desaturase-2 gene, SbDES2 and the sorghum desaturase-3 gene, SbDES3, which consecutively convert 16:1 fatty acids to 16:3 fatty acids having a terminal double bond; a construct containing the genes and their promoter; a vector containing the genes; sorghum fatty acid desaturase-2 protein, SbDES2, and sorghum fatty acid desaturase-3 protein, SbDES3; a method of making SbDES2 protein and SbDES3 protein; a method of transforming plants; and transgenic plants which express SbDES2 and SbDES3 and thereby convert 16:1 fatty acids to 16:3 fatty acids having a terminal double bond in planta.

2. Description of the Relevant Art

Numerous plant species produce phytotoxic secondary metabolites, some of which may play a direct role in allelopathic interactions (Duke et al. 2002. *J. Pesticide Science* 27: 298-306; Inderjit and Duke. 2003. *Planta* 217: 529-539). These interactions often represent a form of chemical warfare occurring between neighboring plants competing for limited light, water, and nutrient resources (Inderjit and Duke, supra; Bais et al. 2004. *Trends Plant Sci.* 9: 26-32). Several sorghum species have been reported to produce phytotoxins which are exuded from root hairs into soil, which suppress the growth of surrounding weeds (Einhellig, F. A. 1996. *Agronomy Journal* 88: 886-893). Numerous studies have contributed to the discovery and identification of the chemicals that are responsible for this observed allelopathic inhibition. Studies on the biologically-active components of both water-soluble and water-insoluble exudates from root hairs of sorghum [*Sorghum bicolor* (L.) Moench] have shown the active role of hydrophobic exudates in the growth inhibition of lettuce seedlings (*Lactuca sativa*) as well as a number of important invasive weed species (Netzly and Butler. 1986. *Crop Science* 26: 775-778). The major component of biologically active root exudes from sorghum root hairs was identified as 2-hydroxy-5-methoxy-3-[8'Z,11'Z)-8',11',14'-pentadecatriene]-p-benzoquinone, referred to as sorgoleone (Chang et al. 1986. *J. Amer. Chem. Soc.* 108: 7858-7860). Considerable effort has subsequently been devoted to the study of the mechanism of phytotoxicity of sorgoleone (Einhellig et al. 1993. *J. Chem. Ecology* 19: 369-375; Einhellig et al. 1992. *J. Chem. Ecology* 18: 1-11; Gonzalez et al. 1997. *J. Agric. Food Chem.* 45: 1415-1421; Nimbal et al. 1996. *J. Agric. Food Chem.* 44: 1343-1347). Early reports on the phytotoxicity of sorgoleone indicated that it is a strong inhibitor of $CO_2$-dependent oxygen evolution in plastids (Einhellig et al. 1993, supra). Further studies on its mode of action have demonstrated that this lipophilic benzoquinone affects both photosynthetic and mitochondrial electron transport (Gonzalez et al., supra; Rasmussen et al. 1992. *J. Chem. Ecology* 18: 197-207; Rimando et al. 1998. *J. Natural Prod.* 61: 927-930; Czarnota et al. 2001. *Weed Technology* 15: 813-825). Sorgoleone also inhibits plant p-hydroxyphenylpyruvate dioxygenase (HPPD; Meazza et al. 2002. *Phytochem.* 60: 281-288), an enzyme that catalyzes the conversion of p-hydroxyphenylpyruvate to homogetisate, which serves as an intermediate in the biosynthesis of plastoquinone (Que and Ho. 1996. *Chem. Rev.* 96: 2607-2624; Matsumoto et al. 2002. *Weed. Biol. Manag.* 2: 39-45). Inhibition of this enzyme leads to the disruption of the biosynthesis of carotenoids, resulting in foliar bleaching, characteristic of chlorophyll loss, and these symptoms are also observed in seedlings grown in the presence of living sorghum root systems (Nimbal et al. 1996. *Pesticide Biochem. Physiol.* 54: 73-83).

The herbicidal and allelopathic properties of sorgoleone make the isolation and characterization of the corresponding genes involved in sorgoleone biosynthesis highly desirable, as manipulation of the pathway in sorghum, or genetic modification of other plant species using these genes could provide important insights into the underlying allelochemical interactions involved.

SUMMARY OF THE INVENTION

We have cloned and expressed SbDES2 and SbDES3, fatty acid desaturase genes from sorghum, and confirmed that their expression results in the production of the enzymes, sorghum desaturase 2 (SbDES2) and sorghum desaturase 3 (SbDES3) and the consecutive conversion of a 16:1 fatty acid to a 16:3 fatty acid having a terminal double bond in vivo and in planta.

In accordance with this discovery, it is an object of the invention to provide isolated nucleic acid molecules which encode the SbDES2 and SbDES3 proteins, enzymes which act consecutively to convert 16:1 fatty acid to 16:3 fatty acid having a terminal double bond.

It is a further object of the invention to provide a construct which encodes the *Sorghum bicolor* desaturase 2 (SbDES2) and sorghum desaturase 3 (SbDES3) proteins.

It is a still further object of the invention to provide a vector which comprises a construct which is capable of expressing said sorghum desaturase genes.

It is an additional object of the invention to provide transgenic plants, plant cells, and seeds containing the nucleic acid construct(s).

It is a another object of the invention to provide a method of transforming the SbDES2 and SbDES3 genes into plants by administering a vector, wherein said vector comprises an effective amount of a nucleic acid construct, which is a DNA sequence capable of transforming the SbDES2 gene into a plant and an effective amount of a nucleic acid construct, which is a DNA sequence capable of transforming the SbDES3 gene into a plant, and whereby said administration of the vector is effective for inducing conversion of 16:1 fatty acid to 16:3 fatty acid in said plant.

It is yet another object of the invention to provide a method of obtaining 16:3 fatty acid having a terminal double bond in plants by stably transforming a plant with isolated nucleotide molecules capable of modulating 16:3 fatty acid content, operably linked with a promoter capable of driving expression of the SbDES2 gene and the SbDES3 gene in a plant cell.

Other objects and advantages of this invention will become readily apparent from the ensuing description.

BRIEF DESCRIPTION OF THE DRAWINGS

FIG. 2A depicts gas chromatograms of fatty acid methyl esters (FAMEs) prepared from immature leaves, mature leaves, mature stems, total root systems, shoot apices, and panicles; FIG. 2B depicts a gas chromatogram of FAMEs prepared from root hair cells, showing the presence of 16:2 and 16:3 fatty acids (FAMEs of authentic standards shown above); FIG. 2C shows the corresponding mass spectrum for 16:2 $\Delta^{9, 12}$ fatty acid identified in root hairs; FIG. 2D shows the corresponding mass spectrum for 16:3 $\Delta^{9, 12, 15}$ fatty acid identified in root hairs.

FIGS. 6A-6C depict gas chromatograms of FAMEs:

FIG. 6A, cells expressing SbDES2, cultured without exogenous fatty acids (inset: FAMEs prepared from yeast transformed with empty vector pYES2); FIG. 6B, cells expressing SbDES3, cultured with exogenous linoleic acid (18:2 $\Delta^{9, 12}$); FIG. 6C, cells co-expressing SbDES2 and SbDES3, cultured without exogenous fatty acids. FIGS. 6D-6F show the mass spectra of corresponding fatty acids produced in transformed yeast cells: FIG. 6D, 16:2 fatty acid from SbDES2-expressing cells; FIG. 6E, 18:3 fatty acid from SbDES3-expressing cells; FIG. 6F, 16:3 fatty acid from cells co-expressing SbDES2 and SbDES3.

FIG. 7A shows the 16:2 DMOX derivative from cells expressing SbDES2. FIG. 7B shows the 18:3 DMOX derivative from cells expressing SbDES3. FIG. 7C shows the mass spectrum of 16:3 DMOX derivative from cells co-expressing SbDES2 and SbDES3.

DETAILED DESCRIPTION OF THE INVENTION

A unique feature of the chemical structure of the allelochemical sorgoleone is the presence of a terminal double bond in the aliphatic side chain, and this characteristic has generated significant interest in the investigation of the sorgoleone biosynthetic pathway. We have identified and isolated novel genes encoding enzymes involved in sorgoleone biosythesis from *Sorghum bicolor* (*S. bicolor* genotype BT X 623). The isolated genes, SbDES2 (SEQ ID NO:1) and SbDES3 (SEQ ID NO:3), from sorghum encode two fatty acid desaturases, SbDES2 and SbDES3, that have been shown in vivo to consecutively convert 16:1 fatty acids to 16:3 fatty acids having a terminal double bond. A $\Delta^{12}$ desaturase (SbDES2; SEQ ID NO:2) converts cis-palmitoleic acid (16:1$\Delta^9$) to hexadecadienoic acid (16:2$\Delta^{9, 12}$), and a $\Delta^{15}$ desaturase (SbDES3; SEQ ID NO:4) is capable of catalyzing the formation of a terminal double bond on a 16:2$\Delta^{9, 12}$ fatty acid, yielding the 16:3$\Delta^{9, 12, 15}$ precursor from which the aliphatic side chain of sorgoleone originates (Fate and Lynn; Dayan et al., supra). Of the three fatty acid desaturases preferentially expressed in root hair cells, both SbDES2 and SbDES3 exhibited activity in the heterologous yeast expression system.

Sorgoleone biosynthesis likely occurs exclusively in root hairs, which appear as cytoplasmically dense cells in sorghum, containing large osmiophilic globules deposited between the plasmalemma and cell wall, presumably associated with sorgoleone rhizosecretion (Czarnota et al. 2003a. *Int. J. Plant Sci.* 164: 861-866; Czarnota et al. 2003b. *J. Chem. Ecology* 29: 2073-2083). Furthermore, the significant quantity of sorgoleone-containing exudates produced by these cells suggests that the corresponding mRNAs encoding these enzymes could be among the most abundant. Therefore, expressed sequence tag (EST) analysis was chosen as a gene isolation strategy to identify genes encoding enzymes involved in the biosynthesis of the allelochemical sorgoleone, as this approach is ideally suited for profiling the more abundant transcripts in a specific cell or tissue type (Ohlrogge and Benning. 2000. *Curr. Opin. Plant Biol.* 3: 224-228; Lange et al., 2000. *Proc. Natl. Acad. Sci. USA* 97: 2934-2939; Guterman et al., 2002. *Plant Cell* 10: 2325-2338; Fridman et al. 2005. *Plant Cell* 17: 1252-1267).

Figure 1:
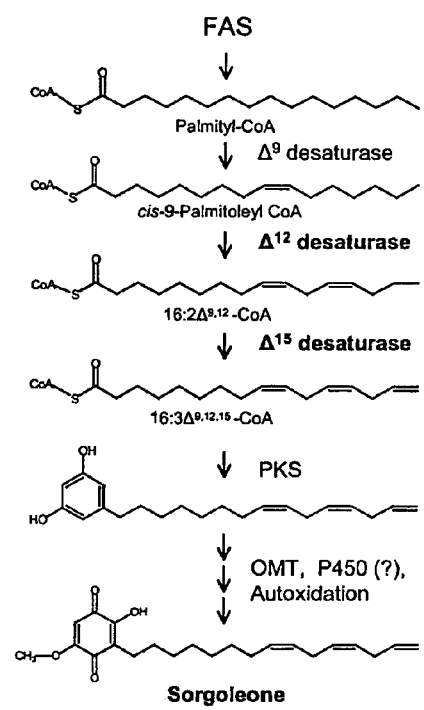
FIG. 1 depicts the proposed pathway for sorgoleone biosynthesis emphasizing reactions catalyzed by fatty acid desaturases (adapted and modified from References (Fate and Lynn. 1996. *J. Amer. Chem. Soc.* 118: 11369-11376; Dayan et al. 2003. *J. Biol. Chem.* 278: 28607-28611).

Labeling studies have demonstrated that the biosynthesis of sorgoleone involves the convergence of the fatty acid and polyketide pathways (Fate and Lynn. 1996. *J. Amer. Chem. Soc.* 118: 11369-11376; Dayan et al., 2003. *J. Biol. Chem.* 278: 28607-28611) through the action of a novel type III polyketide synthase activity utilizing fatty acyl-CoA starter units, resulting in the addition of a quinone head via iterative condensation of acetate extender units (FIG. 1; Cook et al., in preparation). Subsequent modifications of the alkylresorcinol intermediate are likely to be mediated by S-Adenosyl-L-Methionine (SAM)-dependent O-methyltransferases and dihydroxylated by P450 monooxygenases, yielding the reduced form of sorgoleone (a hydroquinone). Upon exudation, the less stable hydroquinone rapidly oxidizes to the highly active benzoquinone form, which can persist in soil for extended periods (Einhellig et al. 1992, supra; Czarnota et al. 2001, supra; Netzly et al. 1988. *Weed Sci.* 36: 441-446). A highly unusual characteristic of the sorgoleone molecule is the presence of a terminal double bond in the aliphatic side chain. To identify the desaturases associated with the sorgoleone biosynthetic pathway, particularly those involved in the terminal bond desaturation of $C_{16}$ fatty acid (FIG. 1), an expressed sequence tag (EST) database containing approximately 5500 sequences randomly selected from a cDNA library prepared from purified *S. bicolor* (genotype BTx623) root hairs cells was mined.

Although the biochemical pathways involved in biosyntheses of many commonly-occurring polyunsaturated fatty acids (PUFAs) in plants have been well characterized (Behrouzian and Buist. 2002. *Curr. Opin. Chem. Biol.* 6: 577-582; Martin et al. 2002. *Biochem. Soc. Trans.* 30: 1080-1082; Wallis et al. 2002. *Trends Biochem. Sci.* 27: 467), to our knowledge, desaturase enzymes capable of performing desaturation reactions producing a terminal double bond have not previously been characterized in a plant system and, in fact, only very recently another system, the free-living soil protozoon *Acanthamoeba castellanii* (Sayanova et al. 2006. *J. Biol. Chem.* 281:36533-36541

Figure 2:
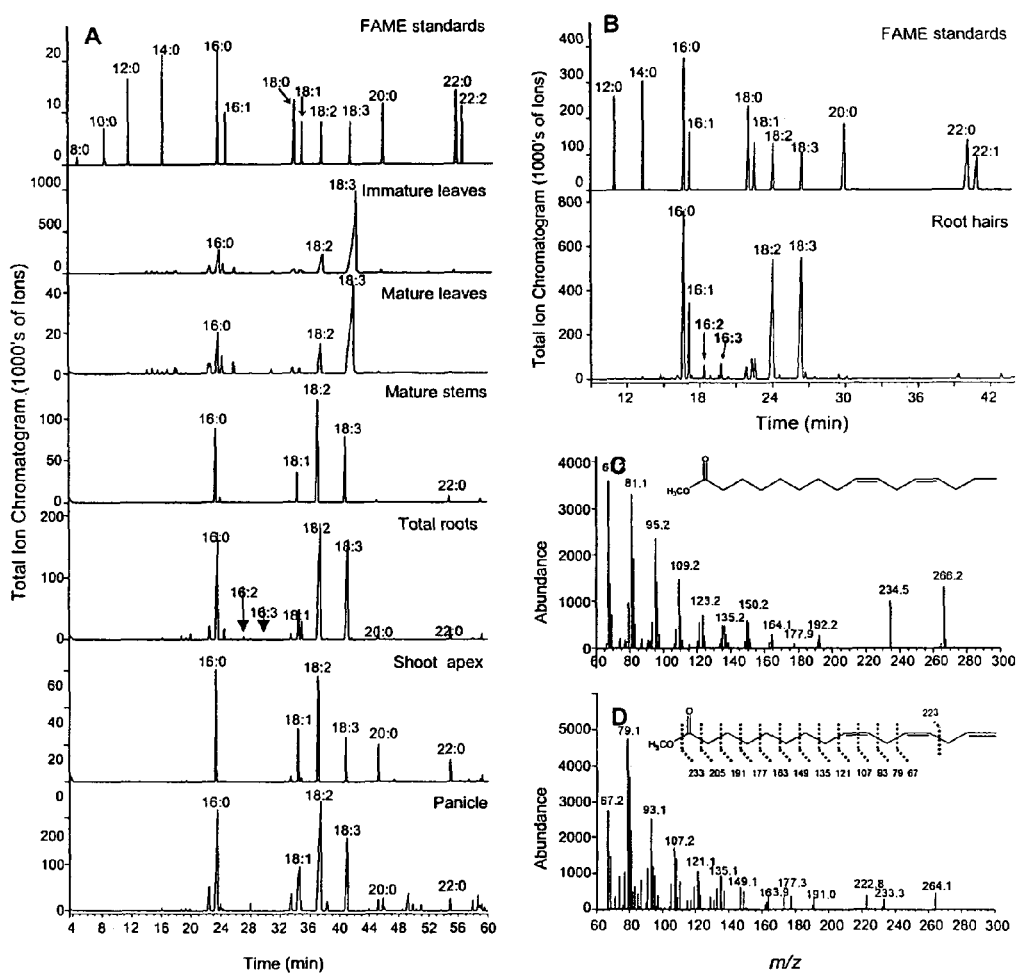
FIGS. 2A-D depict several sorghum fatty acid profiles.

The biosynthesis of the alielochemical sorgoleone is a multi-step process involving both plastidic and cytoplasmic enzymes (Fate and Lynn, supra; Dayan et al., supra). One of the key steps is the formation of hexadecatrienoic acid (16:$3\Delta^{9,12,15}$), an unsaturated fatty acid proposed to serve as a precursor for the associated polyketide synthase in the pathway. To examine the presence and distribution of $16:2\Delta^{9,12}$ and $16:3\Delta^{9,12,15}$ in sorghum, the fatty acid composition of various tissues (mature and immature leaves, stems, shoot apices, panicles, and whole root systems) were analyzed (FIG. 2A). The predominance of palmitic (16:0), linoleic (18:2), and linolenic (18:3) acids was observed in all sorghum tissues. A trace of 16:2 (peak at 27.0 min and 18:3 (peak at 29.7 min) were observed in the chromatograms of extracted roots, as indicated by mass spectral data (not shown), however, the low levels for these peaks precluded their unequivocal identification. As sorgoleone is a major component in the oily exudate droplets associated with sorghum root hairs, root hairs were also isolated and analyzed for the presence of the precursor $C_{16}$ fatty acids. Two peaks (corresponding to 16:2 and 16:3 fatty acid) were detected in the lipid extracts (FIG. 2B) by GC/MS. The mass spectrum (FIG. 2C) of the fatty acidmethyl ester (FAME) corresponding to the 16:2 peak (FIG. 2B) exhibited a prominent molecular ion at m/z=266.2, characteristic of a 16.2 methyl ester and identical to that of methyl 9,12-hexadecadienoate (methyl ester and identical to that of methyl 9,12-hexadecadienoate (Retrieved from the Internet: <URL: lipidiibrary.co.uk/masspec.html), whereas the spectrum of the second peak corresponding to 16:3 (FIG. 26) had a molecular ion at m/z=264.1, and a fragmentation pattern consistent with hexadecatrienoate possessing a terminal methylene (FIG. 2D). Collectively, these data identify the $16:2\Delta^{9,12}$ and $16:3\Delta^{9,12,15}$ fatty acids in root hairs, and furthermore, strongly suggest that these precursors are primarily synthesized in root hair cells.

Numerous reports have demonstrated that plant FAD2 desaturases expressed in yeast are capable of introducing a double bond at the Δ12 position using endogenous palmitoleic acid ($16:1\Delta^9$) and oleic acid ($18:1\Delta^9$) as substrates. The activity of these enzymes frequently involves the M2 desaturation of pamitoleic and oleic acids to produce hexadecadeinoic acid ($16:2^{9,12}$) and linoleic acid ($18:2\Delta^{9,12}$), respectively (Cahoon et al. 2004. *J. Biol. Chem.* 279: 12495-12502; Covello & Reed. 1996. *Plant Physiol.* 111: 223-226; Dyer et al., supra; Domergue et al. 2003. *Plant Physiol.* 131: 1648-1660).

Detailed analysis of SbDES3 activity upon in vivo substrates present in an engineered yeast system indicated that the enzyme exhibits the capacity to synthesize the $16:3\Delta^{9,12,}$ 15 fatty acid considered to be the starter molecule used by polyketide synthases in the sorgoleone biosynthetic pathway. This is the first fatty acid desaturase described to date that exhibits terminal desaturase activity in plants. Furthermore, the tissue-specific accumulation of SbDES2 and SbDES3 correlated with the accumulation of 16:2 and 16:3 fatty acids in root hairs as analyzed by GC/MS, suggesting the likely participation of these enzymes in the biosyntheses of sorgoleone.

The terms "nucleic acid molecule", "nucleic acid sequence", "polynucleotide", "polynucleotide sequence", "nucleic acid fragment", "isolated nucleic acid fragment" are used interchangeably herein. These terms encompass nucleotide sequences and the like. A polynucleotide may be a polymer of RNA or DNA that is single- or double-stranded and that optionally contains synthetic, non-natural or altered nucleotide bases. A polynucleotide in the form of a polymer of DNA may be comprised of one or more segments of cDNA, genomic DNA, synthetic DNA, or mixtures thereof.

The term "isolated" polynucleotide refers to a polynucleotide that is substantially free from other nucleic acid sequences, such as other chromosomal and extrachromosomal DNA and RNA, that normally accompany or interact with it as found in its naturally occurring environment. However, isolated polynucleotides may contain polynucleotide sequences which may have originally existed as extrachromosomal DNA but exist as a nucleotide insertion within the isolated polynucleotide. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

As used herein, "recombinant" refers to a nucleic acid molecule which has been obtained by manipulation of genetic material using restriction enzymes, ligases, and similar genetic engineering techniques as described by, for example, Sambrook et al. 1989. Molecular Cloning: A Laboratory Manual, Second Edition, Cold Spring Harbor Laboratory Press, Cold Spring Harbor, N.Y. or DNA Cloning: A Practical Approach, Vol. I and II (Ed. D. N. Glover), IRL Press, Oxford, 1985. "Recombinant," as used herein, does not refer to naturally occurring genetic recombinations.

As used herein, the term "chimeric" refers to two or more DNA molecules which are derived from different sources, strains, or species, which do not recombine under natural conditions, or to two or more DNA molecules from the same species, which are linked in a manner that does not occur in the native genome. A "construct" or "chimeric gene construct" refers to a nucleic acid sequence encoding a protein, here the SbDES2 and SbDES3 enzymes, operably linked to a promoter and/or other regulatory sequences.

As used herein, the term "express" or "expression" is defined to mean transcription alone. The regulatory elements are operably linked to the coding sequence of the SbDES2 and SbDES3 genes such that the regulatory element is capable of controlling expression of the SbDES2 and SbDES3 genes. "Altered levels" or "altered expression" refers to the production of gene product(s) in transgenic organisms in amounts or proportions that differ from that of normal or non-transformed organisms.

As used herein, the terms "encoding", "coding", or "encoded" when used in the context of a specified nucleic acid mean that the nucleic acid comprises the requisite information to guide translation of the nucleotide sequence into a specified protein. The information by which a protein is encoded is specified by the use of codons. A nucleic acid encoding a protein may comprise non-translated sequences (e.g., introns) within translated regions of the nucleic acid or may lack such intervening non-translated sequences (e.g., as in cDNA).

The term "operably linked" refers to the association of two or more nucleic acid fragments on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

"Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence that can stimulate promoter activity and may be an innate element of the promoter or a heterologous element inserted to enhance the level or tissue-specificity of a promoter. Promoters may be derived in their entirety from a native gene or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions. The tissue-specificity of a promoter, for example, is exemplified by the promoter sequence which specifically induces the SbDES2 and SbDES3 genes expression in root hairs and roots. Promoters that cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg. 1989. Biochemistry of Plants 15:1-82. It is further recognized that since in most cases the exact boundaries of regulatory sequences have not been completely defined, nucleic acid fragments of different lengths may have identical promoter activity.

The "translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency.

The "3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor.

"RNA transcript" refers to the product resulting from RNA polymerase-catalyzed transcription of a DNA sequence. When the RNA transcript is a perfect complementary copy of the DNA sequence, it is referred to as the primary transcript or it may be an RNA sequence derived from posttranscriptional processing of the primary transcript and is referred to as the mature RNA. "Messenger RNA (mRNA)" refers to the RNA that is without introns and that can be translated into polypeptides by the cell. "cDNA" refers to a DNA that is complementary to and derived from an mRNA template. The cDNA can be single-stranded or converted to double stranded form using, for example, the Klenow fragment of DNA polymerase I. "Sense" RNA refers to an RNA transcript that includes the mRNA and so can be translated into a polypeptide by the cell. "Antisense", when used in the context of a particular nucleotide sequence, refers to the complementary strand of the reference transcription product. "Antisense RNA" refers to an RNA transcript that is complementary to all or part of a target primary transcript or mRNA and that blocks the expression of a target gene. The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

As used herein, the term "expressed sequence tag" (EST) refers to a short strand of DNA (approximately 200 base pairs long) which is part of a cDNA. ESTs provide an indication of the abundance of the genes that are being expressed in that tissue at that stage of development. Because an EST is usually unique to a particular cDNA, and because cDNAs correspond to a particular gene in the genome, ESTs can be used to help identify unknown genes and to map their position in the genome.

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include *Agrobacterium*-mediated transformation (De Blaere et al. 1987. *Meth. Enzymol.* 143:277) and particle-accelerated or "gene gun" transformation technology (Klein et al. 1987. *Nature (London)* 327:70-73; U.S. Pat. No. 4,945,050, incorporated herein by reference). Additional transformation methods are disclosed below. Thus, isolated polynucleotides of the present invention can be incorporated into recombinant constructs, typically DNA constructs, capable of introduction into and replication in a host cell. Such a construct can be a vector that includes a replication system and sequences that are capable of transcription and translation of a polypeptide-encoding sequence in a given host cell. A number of vectors suitable for stable transfection of plant cells or for the establishment of transgenic plants have been described in, e.g., Pouwels et al. 1985. Supp. 1987. *Cloning Vectors: A Laboratory Manual*; Weissbach and Weissbach. 1989. *Methods for Plant Molecular Biology*, Academic Press, New York; and Flevin et al. 1990. *Plant Molecular Biology Manual*, Kluwer Academic Publishers, Boston. Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

A "protein" or "polypeptide" is a chain of amino acids arranged in a specific order determined by the coding sequence in a polynucleotide encoding the polypeptide. Each protein or polypeptide has a unique function.

The term "substantially pure" as used herein refers to the SbDES2 and SbDES3 polypeptides that are substantially free of other proteins, lipids, carbohydrates or other materials with which it is naturally associated. One skilled in the art can purify SbDES2 and SbDES3 polypeptides using standard techniques for protein purification. The purity of the SbDES2 and SbDES3 polypeptides can also be determined by amino-terminal amino acid sequence analysis.

The invention includes functional SbDES2 and SbDES3 polypeptides and functional fragments thereof, as well as mutants and variants having the same biological function or activity. As used herein, the terms "functional fragment", "mutant" and "variant" refers to a polypeptide which possesses biological function or activity identified through a defined functional assay and associated with a particular biologic, morphologic, or phenotypic alteration in the cell. The term "functional fragments of SbDES2 and/or SbDES3 polypeptide(s)", refers to all fragments of SbDES2 and/or SbDES3 that retain SbDES2 and SbDES3 activity and function in the sorgoleone biosynthetic pathway. Functional fragments, for example, can vary in size from a polypeptide fragment as small as an epitope capable of binding an antibody molecule, to a large polypeptide capable of participating in the characteristic induction or programming of phenotypic changes within a cell. Furthermore, the function or activity of SbDES2 and SbDES3 in the sorgoleone pathway can be utilized in bioassays to identify functional fragments of SbDES2 and SbDES3 polypeptides or related polypeptides.

Modifications of the SbDES2 and SbDES3 primary amino acid sequences may result in further mutant or variant proteins having substantially equivalent activity to the SbDES2 and SbDES3 polypeptides described herein. Such modifications may be deliberate, as by site-directed mutagenesis, or may occur by spontaneous changes in amino acid sequences where these changes produce modified polypeptides having substantially equivalent activity to the SbDES2 and SbDES3 polypeptides. Any polypeptides produced by minor modifications of the SbDES2 and SbDES3 primary amino acid sequences are included herein as long as the biological activity of SbDES2 and SbDES3 is present; e.g., having a role in the consecutive conversion of a 16:1 fatty acid to a 16:3 fatty acid having a terminal double bond in vivo and in planta and/or a role in pathways leading to sorgoleone accumulation in plants.

A heterologous coding sequence refers to coding sequences which encode peptides or proteins, unrelated to, or, other than, the SbDES2 and SbDES3 polypeptides provided above and which are not intrinsically found in the position provided in the chimeric gene construct.

Genes encoding SbDES2 and SbDES3 protein can be cloned using a variety of techniques according to the invention. The simplest procedure for the cloning of SbDES2 and SbDES3 genes requires the cloning of genomic DNA from an organism identified as producing the SbDES2 and SbDES3 proteins, and the transfer of the cloned DNA on a suitable plasmid or vector to a host organism which does not produce the SbDES2 and SbDES3 proteins, followed by the identification of transformed hosts to which the ability to produce the SbDES2 and SbDES3 proteins have been conferred. The transforming SbDES2- and SbDES3-conferring DNA can be cleaved into smaller fragments and the smallest which maintains the SbDES2- and SbDES3-conferring ability can be further characterized. Techniques suitable for cloning by homology include standard library screening by DNA hybridization or polymerase chain reaction (PCR) amplification using primers derived from conserved sequences. As defined herein, two DNA sequences are substantially homologous when at least 80% (preferably at least 85% and most preferably 90%) of the nucleotides match over the defined length of the sequence using algorithms such as CLUSTRAL or PILEUP. Sequences that are substantially homologous can be identified in a Southern hybridization experiment under stringent conditions as is known in the art. See, for example, Sambrook et al., supra. Sambrook et al. describe highly stringent conditions as a hybridization temperature 5-10° C. below the $T_m$ of a perfectly matched target and probe; thus, sequences that are "substantially homologous" would hybridize under such conditions.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to modifications of the nucleic acid fragments of the instant invention such as deletion or insertion of nucleotides that do not substantially affect the functional properties of the resulting transcript. It is therefore understood that the invention encompasses more than the specific exemplary nucleotide or amino acid sequences and includes functional equivalents thereof. Alterations in a nucleic acid fragment that result in the production of a chemically equivalent amino acid at a given site, but do not affect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products. A method of selecting an isolated polynucleotide that affects the level of expression of a polypeptide in a virus or in a host cell (eukaryotic, such as plant, yeast, fungi, or algae; prokaryotic, such as bacteria) may comprise the steps of: constructing an isolated polynucleotide of the present invention or an isolated chimeric gene of the present invention; introducing the isolated polynucleotide or the isolated chimeric gene into a host cell; measuring the level of a polypeptide in the host cell containing the isolated polynucleotide; and comparing the level of a polypeptide in the host cell containing the isolated polynucleotide with the level of a polypeptide in a host cell that does not contain the isolated polynucleotide.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (1985. Nucleic Acid Hybridization, Hames and Higgins, Eds., IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms.

Thus, isolated sequences that encode SbDES2 and SbDES3 polypeptides and which hybridize under stringent conditions, as described herein, to the SbDES2 and SbDES3 sequences disclosed herein, or to fragments thereof, are encompassed by the present invention. Fragments of a nucleotide sequence that are useful as hybridization probes may not encode fragment proteins retaining biological activity.

Substantially similar nucleic acid fragments of the instant invention may also be characterized by the percent identity of the amino acid sequences that they encode to the amino acid sequences disclosed herein, as determined by algorithms commonly employed by those skilled in this art.

Methods of alignment of sequences for comparison are well known in the art. Thus, the determination of percent identity between any two sequences can be accomplished using a mathematical algorithm. Non-limiting examples of such mathematical algorithms are the algorithm of Myers and Miller (1988. *CABIOS* 4:11-17), the local homology algorithm of Smith et al. (1981. *Adv. Appl. Math.* 2:482); the homology alignment algorithm of Needleman and Wunsch (1970. *J. Mol. Biol.* 48:443-453); the search-for-similarity-method of Pearson and Lipman (1988. *Proc. Natl. Acad. Sci.* 85:2444-2448; the algorithm of Karlin and Altschul (1990. *Proc. Natl. Acad. Sci. USA* 87:2264), modified as in Karlin and Altschul (1993. *Proc. Natl. Acad. Sci. USA* 90:5873-5877).

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters.

As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins, it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule.

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

The term "substantial identity" of polynucleotide sequences means that a polynucleotide comprises a sequence that has at least 80% sequence identity, preferably at least 85%, more preferably at least 90%, most preferably at least 95% sequence identity compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 80%, preferably at least 85%, more preferably at least 90%, and most preferably at least 95%. Preferably, optimal alignment is conducted using the homology alignment algorithm of Needleman et al. (1970. *J. Mol. Biol.* 48:443).

Another indication that nucleotide sequences are substantially identical is if two molecules hybridize to each other under stringent conditions. Generally, stringent conditions are selected to be about 5° C. lower than the thermal melting point (Tm) for the specific sequence at a defined ionic strength and pH. However, stringent conditions encompass temperatures in the range of about 1° C. to about 20° C., depending upon the desired degree of stringency as otherwise qualified herein.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST. In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification and isolation. In addition, short oligonucleotides of 12 or more nucleotides may be use as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise a particular plant protein. The skilled artisan, having the benefit of the sequences as reported herein, may now use all or a substantial portion of the disclosed sequences for purposes known to those skilled in this art. For example, that portion of the SbDES2 and SbDES3 proteins beginning with amino acid 57, i.e., serine, and consisting of 19 contiguous amino acids or less (as described above), can be used to identify or isolate the SbDES2 and SbDES3 genes encoding said SbDES2 and SbDES3 proteins in nucleotide sequences of plants other than sorghum. Thus, such a portion represents a "substantial portion" and can be used to establish "substantial identity", i.e., sequence identity of at least 80%, compared to the reference sequence, sorghum. Accordingly, the instant invention comprises the complete sequences as reported in the accompanying Sequence Listing, as well as substantial portions at those sequences as defined above.

By "variants" substantially similar sequences are intended. For nucleotide sequences, conservative variants include those sequences that, because of the degeneracy of the genetic code, encode the amino acid sequence of each of the SbDES2 and SbDES3 polypeptides of the invention. Naturally occurring allelic variants such as these can be identified with the use of well-known molecular biology techniques, as, for example, with polymerase chain reaction (PCR), a technique used for the amplification of specific DNA segments. Generally, variants of a particular nucleotide sequence of the invention will have generally at least about 90%, preferably at least about 95% and more preferably at least about 98% sequence identity to that particular nucleotide sequence as determined by sequence alignment programs described elsewhere herein.

By "variant protein" a protein derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein is intended. Variant proteins encompassed by the present invention are biologically active, that is they possess the desired biological activities, that is, SbDES2 and SbDES3 activities as described herein. Such variants may result from, for example, genetic polymorphism or from human manipulation. Biologically active variants of native SbDES2 and SbDES3 proteins of the invention will have at least about 90%, preferably at least about 95%, and more preferably at least about 98% sequence identity to the amino acid sequence for the native protein as determined by sequence alignment programs described elsewhere herein. A biologically active variant of a protein of the invention may differ from that protein by as few as 1-15 amino acid residues, or even one amino acid residue.

The polypeptides of the invention may be altered in various ways including amino acid substitutions, deletions, truncations, and insertions. Novel proteins having properties of interest may be created by combining elements and fragments of proteins of the present invention, as well as with other proteins. Methods for such manipulations are generally known in the art. Thus, the genes and nucleotide sequences of the invention include both the naturally occurring sequences as well as mutant forms. Likewise, the proteins of the invention encompass naturally occurring proteins as well as variations and modified forms thereof. Such variants will continue to possess the desired SbDES2 and SbDES3 activities. Obviously, the mutations that will be made in the DNA encoding the variant must not place the sequence out of reading frame and preferably will not create complementary regions that could produce secondary mRNA structure.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays where the effects of the SbDES2 and SbDES3 proteins can be observed.

"Codon degeneracy" refers to divergence in the genetic code permitting variation of the nucleotide sequence without affecting the amino acid sequence of an encoded polypeptide. Accordingly, the instant invention relates to any nucleic acid fragment comprising a nucleotide sequence that encodes all or a substantial portion of the amino acid sequences set forth herein.

It is to be understood that as used herein the term "transgenic" includes any cell, cell line, callus, tissue, plant part, or plant the genotype of which has been altered by the presence of a heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

As used herein, the term "plant" includes reference to whole plants, plant organs (e.g., leaves, stems, roots, etc.), seeds, plant cells, and progeny of same. Parts of transgenic plants are to be understood within the scope of the invention to comprise, for example, plant cells, protoplasts, tissues, callus, embryos as well as flowers, stems, fruits, leaves, roots originating in transgenic plants or their progeny previously transformed with a DNA molecule of the invention and therefore consisting at least in part of transgenic cells, are also an object of the present invention.

As used herein, the term "plant cell" includes, without limitation, seeds, suspension cultures, embryos, meristematic regions, callus tissue, leaves, roots, shoots, gametophytes, sporophytes, pollen, and microspores. The class of plants that can be used in the methods of the invention is generally as broad as the class of higher plants amenable to transformation techniques, including both monocotyledonous and dicotyledonous plants.

The successful cloning of SbDES2 and SbDES3 is a major technological advancement. SbDES2 and SbDES3 can be used to form unusual $16:3\Delta^{9, 12, 15}$ fatty acids which possesses a terminal double bond. The generation of sorgoleones is complex and involves many intermediaries; however, as more information becomes available and additional biosynthetic enzymes become identified, SbDES2 and SbDES3 may additionally be used to increase the accumulation of sorgoleones in the root hairs and roots of sorghum and other food crops to ensure the suppression of weeds and thus higher yields of food crops.

EXAMPLES

Having now generally described this invention, the same will be better understood by reference to certain specific examples, which are included herein only to further illustrate the invention and are not intended to limit the scope of the invention as defined by the claims.

Example 1

Plant Materials

Mature leaves, stems, and emerging panicles were harvested from approximately 2-month-old, greenhouse-grown *Sorghum bicolor* (cv. BTx623) plants. Immature leaves and shoot apices were isolated from 8-day-old BTx623 seedlings maintained in a growth chamber at 28° C., 16 hr light/8 hr dark, 400 µmol/m² sec intensity. Total root systems and root hairs were isolated from 8-day-old seedlings grown using a capillary mat system (Czarnota et al. 2003b, supra). All tissues were collected, then flash-frozen in liquid nitrogen, and stored at −80° C. prior to extraction. Root hairs were isolated according to the method of Bucher et al. (1997. *Plant Mol. Biol.* 35: 497-508).

Example 2

RNA Isolation and Quantitative Real-Time RT-PCR

Figures 3, 4:
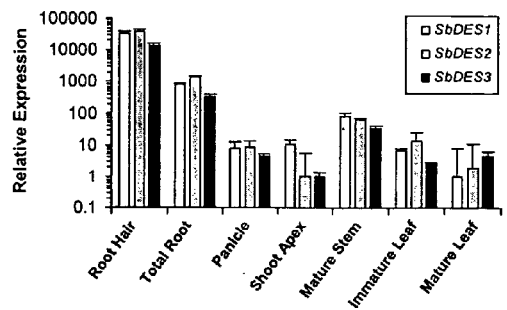
FIG. 3 shows the identification of root-hair-specific fatty acid desaturase-like (FAD-like) ESTs in sorghum. Relative expression levels of three FAD-like sequences were determined in different sorghum tissues by quantitative real-time RT-PCR using gene-specific primers. Data were normalized to an internal control (18S rRNA), and the $\Delta\Delta C_T$ method was used to obtain the relative expression level for each sequence. Data are expressed as mean±SD.
FIG. 4 shows the sequence alignment of SbDES1, SbDES2, and SbDES3 with related plant FADs. Amino acid sequences were aligned using ClustalW. The three conserved histidine motifs are indicated, and the predicted transmembrane domains denoted by dashed lines. Identical and similar amino acids are shaded with black and gray, respectively. Abbreviations: AtFAD2, *Arabidopsis thaliana* FAD2 (Accession number: AAM98321); TaFAD3, *Triticum aestivum* (Accession number: BAA28358).

Total RNAs for real-time PCR experiments shown in FIG. 3 were isolated from 50 mg of flash-frozen, pulverized 10-day-old BTx623 seedling tissues using an RNeasy Plant Mini-Kit (Qiagen, Valencia, Calif.). Quantitative real-time RT-PCR (QRT-RTPCR) reactions were performed in triplicate using a GenAmp® 5700 Sequence Detection System (Applied Biosystems, Foster City, Calif.) as previously described (Baerson et al. 2005. *J. Biol. Chem.* 280: 21867-21881).

Example 3

Isolation of *Sorghum* cDNA Clones

To isolate full-length cDNA clones corresponding to the identified root-hair specific genes, primers were made against the EST sequences and used for both 5'- and 3'-rapid amplification of cDNA ends (RACE) using total RNA extracted from sorghum root hairs using the BD SMART® RACE cDNA Amplification Kit (BD Biosciences Clontech, Palo Alto, Calif.) according to the manufacturer's instructions. Primer sets for 5'- and 3'-RACE were 2A03: 5'-CCAAG-GAGGTGAAGTGGCAG-3' (SEQ ID NO:5) and 5'-ATAC-TACCGGGAGCCACACAAG-3'(SEQ ID NO:6); 25B05: 5'-TCGCTGACGAAATGGTTGAC-3'(SEQ ID NO:7) and 5'CCTCCTTGGCGTGTT CCTC-3'(SEQ ID NO:8); 56D10: 5'-TGGACGATCACCTCAATCCTG-3' (SEQ ID NO:9) and 5'-CAACAAGTTCTAGCTGCTTGATGC-3'(SEQ ID NO:10), respectively. Products of the RACE amplifications were resolved on agarose gels, cloned into the pCR®4-TOPO vector (Invitrogen, Carlsbad, Calif.), and then confirmed by sequence analysis. Full-length cDNA sequences of each gene were then confirmed by PCR using primer pairs complementary to the 5' and 3' ends of each open reading frame (ORF), based on the sequence data identified in RACE experiments, using Pfu thermostable DNA polymerase (Stratagene, La Jolla, Calif.) and first-strand cDNA generated from RNA extracted from sorghum root hairs. Several independent isolates from each amplification were sequenced to ensure the authenticity of the ORFS.

Example 4

Identification and Cloning of Fatty Acid Desaturases from *Sorghum*

To identify the desaturases associated with the sorgoleone biosynthetic pathway, particularly those involved in the terminal bond desaturation of $C_{16}$ fatty acid (FIG. 1), an EST database generated using a cDNA library prepared from isolated sorghum root hair cells was mined. Database mining were performed both by using the Magic Gene Discovery software (Pratt at al. 2004. *Plant Physiol.* 139: 869-884) and by BLAST analysis (Retrieved from the Internet: <URL: ncbi.nlm.nih.gov/BLAST). From these analyses, 47 desaturase-like ESTS were identified, which assembled into 11 unique contigs. Quantitative real-time RT-PCR analysis showed that three out of the 11 unique desaturase sequences (suggested by clustering) were preferentially expressed in root hair cells (FIG. 3). The corresponding full-length cDNA clones were isolated using cDNA prepared from root hair cells, and designated SbDES1 (SEQ ID NO:11), SbDES2 and SbDES3. The protein sequences deduced from SbDES3 and SbDES1 were 90% identical to each other, and shared only 33.7% and 33.8% identity, respectively, with the sequence from SbDES2. BLAST analysis of these protein sequences revealed that both SbDES3 and SbDES1 (SEQ ID NO:12) exhibited significant similarity to known plant fatty acid desaturase (FAD3-type) sequences, and SbDES2 displayed a high degree of similarity to plant FAD2-type sequences (Los and Murata. 1998. *Biochim. Biophys. Acta* 1394: 3-15; Shanklin and Cahoon. 1998. *Annu. Rev. Plant Physiol. Plant Mol. Biol.* 49: 611-641). A previously isolated putative desaturase clone from the *S. bicolor* X *S. sudanense* hybrid, SX17 (Yang et al. 2004. *J. Exp. Botany* 55: 2251-2259) showed homology to the SbDES3 clone described here. Based on comparisons to known fatty acid desaturases, the predicted protein sequences of all three cDNAs exhibited all of the main structural characteristics possessed by fatty acid desaturases from other systems (Los and Murata, Shanklin and Cahoon, supra) notably the predicted transmembrane domains and three highly conserved histidine-rich motifs occurring in most membrane-bound desaturases (FIG. 4). The conserved histidine-rich motifs are believed to be required for fatty acid desaturase activity (Shanklin at al. 1994. *Biochem.* 33: 12787-12794).

Figure 5:
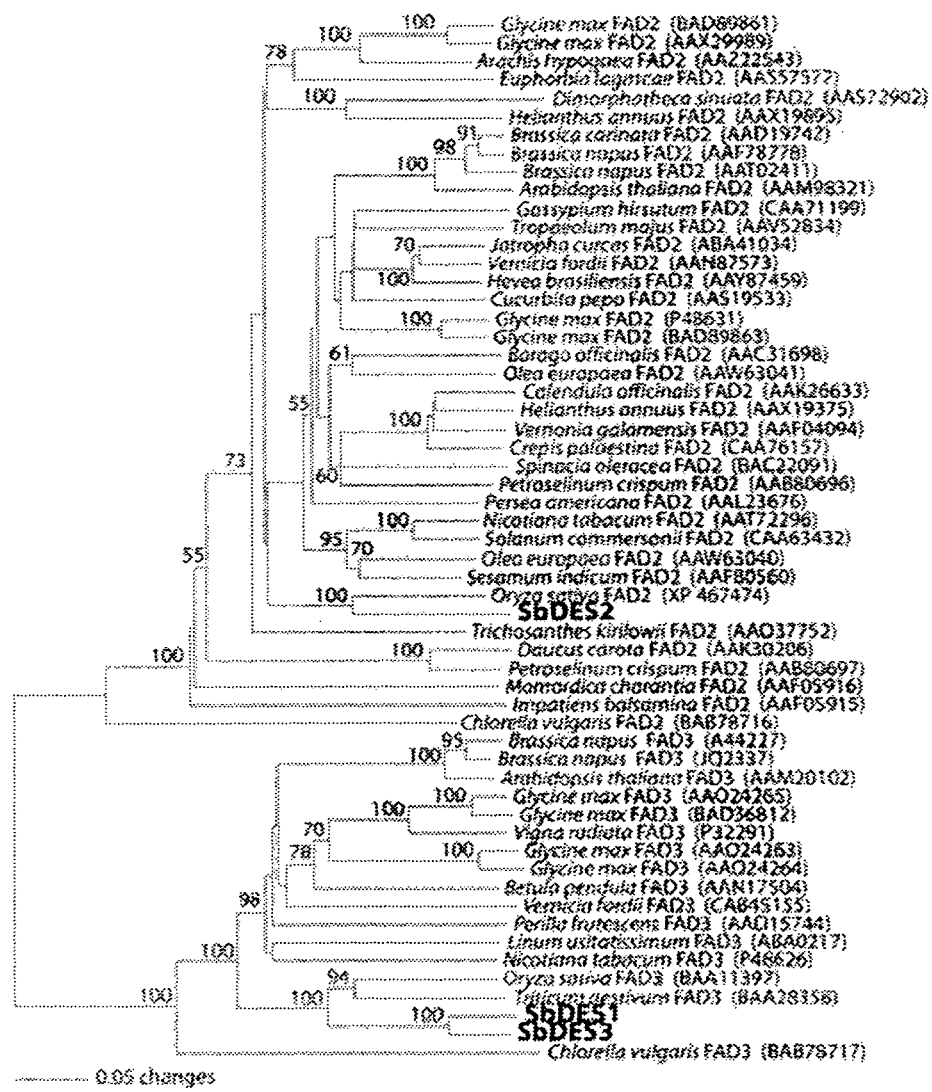
FIG. 5 shows a phylogenetic analysis of SbDES1, SbDES2, and SbDES3 relatives. The phylogram was generated using the neighbor-joining method as implemented in PAUP ver 4.0b10. The bootstrap method was performed for 5000 pseudoreplicate data sets. Numbers shown at the tree forks indicate frequency of occurrence among all bootstrap iterations performed.

These comparisons were further supported by phylogenetic analysis (FIG. 5; Example 5). SbDES2 was most closely related to members of the plant microsomal FAD2-type desaturase subfamily which, among those functionally characterized, typically desaturate $C_{16}/C_{18}$ acyl chains at the $\Delta^{12}$ position. In contrast, both SbDES1 and SbDES3 were positioned within the group corresponding to the plant microsomal FAD3-type desaturases, which mainly catalyze the conversion of 18:2 to 18:3 in phospholipids (Browse et al. 1993. *J. Biol. Chem.* 268: 16345-16351). For example, the closely related FAD3-like enzymes from wheat and rice (accession numbers: BAA28358 and BAA11397—FIG. 5) catalyze the conversion of linoleic acid ($18:2\Delta^{9,12}$) to linolenic acid ($18:3\Delta^{9,12,15}$; Kodama et al. 1997. *Plant Mol. Biol.* 33: 493-502; Horiguchi et al. 2000. *Plant J.* 24: 805-813).

Example 5

Phylogenetic Analysis

Amino acid sequences of putative homology to fatty acid desaturases were retrieved from Genbank using BLAST with default parameters. A candidate list was screened for redundancy and errors, and a data set was assembled from 54 sequences, in addition to the three sequences characterized here (SbDES1, SbDES2, and SbDES3). Sequences of the Chlorophyte, *Chlorella vulgaris*, were included to aid in rooting the estimated phylogeny. Multiple sequence alignments were constructed with ClustalX ver. 1.81 (Thompson et al. 1997. *Nucleic Acids Res.* 25: 4876-4882). Three parameter sets were investigated to assess sensitivity of the alignment to gap costs: default (gap opening=10.0, gap extension=0.2); gap opening=10.0, gap extension=1.0; gap opening=1.0, gap extension=1.0. All other parameters were set at default values (in particular, the Gonnet weight matrix was employed). The alignments differed somewhat in length (463, 464, and 482 residues, respectively).

Phylogenetic estimates of the relationships among sequences were conducted separately for each alignment. The neighbor-joining method (Saitou and Nei. 1987. Mol. Biol. Evol. 4: 406-425) as implemented in PAUP* ver. 4.0b10 (Swofford, supra) was used to estimate trees. Default parameters were used except that ties were broken randomly. Trees were midpoint rooted and nodal support was estimated by the bootstrap (Felsenstein, J. 1985. *Evolution* 39: 783-791), employing 5000 pseudoreplicate data sets. Phylogenetic trees estimated from the three alignments were extremely similar. The second alignment, with a 10:1 ratio of gap opening to extension penalties, was selected for discussion and further analysis. However, all interpretations made here would be identical on trees estimated from the other two alignments (not shown).

Example 6

Plasmid Construction for Heterologous Expression in *S. cerevisiae*

For heterologous expression in yeast, open reading frames were cloned as HindIII/XhoI fragments 3' to the galactose-inducible GAL1 promoter into the yeast expression vector pYES2 (Invitrogen), yielding the plasmids pYE25B (for SbDES1 overexpression), pYE56D (for SbDES2 overexpression) and pYE2A (for SbDES3 overexpression). All three constructs were then transformed into yeast strain INVSc1 using the lithium acetate method (Burke et al. 2000. *Methods in Yeast Genetics*, CSHL Press, NY, pages 103-105). The resulting transformants were cultivated in the presence and absence of exogenously supplied palmitic (16:0), palmitoleic (16:1$\Delta^9$), linoleic (18:2$\Delta^{9, 12}$), α-linolenic (18:3$\Delta^{9, 12, 15}$), or γ-linolenic acid (18:3$\Delta^{6, 9, 12}$). As a control, strains harboring the empty pYES2 vector were cultured in parallel. Following 48 hour incubations, the cells were harvested, lipids were extracted, and fatty acid compositions were determined by GC/MS analysis of fatty acid methyl ester derivatives.

Figure 6:
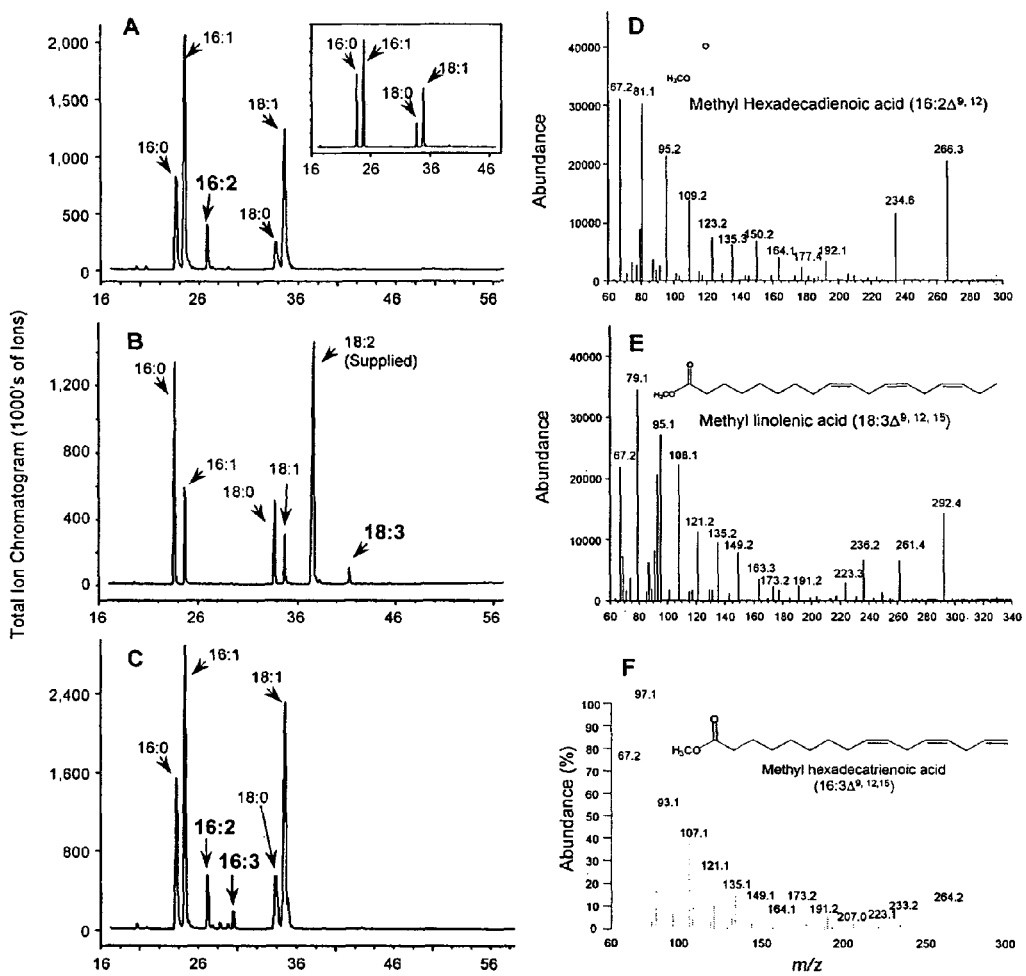
FIGS. 6A-F depict GAC/MS Analyses of FAMEs prepared from yeast cells expressing *S. bicolor* desaturases, cultured in the presence and absence of exogenously supplied fatty acids.

Culture Conditions and Recombinant Protein Expression: Transformed yeast cells were grown in synthetic medium (SC-Ura) containing 2% (w/v) glucose as carbon source and 0.67% (w/v) yeast nitrogen base without amino acids. In the case of co-expression, transformed yeast cells were grown in similar media lacking histidine (SC-UH) for the selection of pRS423. Induction of recombinant protein expression was performed as described by Dyer et al. (2002. *Plant Physiol.* 130:2027-2038): briefly, overnight cultures were pelleted by centrifugation, and resuspended in induction medium (2% [w/v] galactose, 0.67% [w/v] yeast nitrogen base without amino acids, and 0.1% [v/v] tergitol NP-40 (Sigma, St. Louis, Mo.)). The cells then were diluted in 20 ml of the same medium to obtain an $ODD_{600}$ of 0.4. Exogenous free fatty acids (Sigma), when included, were added to the diluted cells at a final concentration of 0.1% (v/v). Yeast cell lines, including 'empty vector' controls, were induced at 20° C. for 48 hr prior to harvest, both in the absence or presence of exogenous fatty acids added to cultures at a final concentration of 0.1% (v/v): palmitic acid, palmitoleic acid, oleic acid, linoleic acid, γ-linolenic acid and α-linolenic acid (Sigma). For SbDES2 and SbDES3 co-expression experiments, yeast cultures were maintained at 30° C. to obtain optimal yields of the 16:3$\Delta^{9, 12, 15}$ product (FIG. 6 C, F). Cells were grown for 42 h at 20° C. with shaking at 300 rpm prior to harvesting. Yeast cells were harvested by centrifugation at 6,500×g for 10 min, washed three times with 0.1 M $NaHCO_3$, flash-frozen in liquid nitrogen, then stored at −80° C. until use.

Fatty Acid Extraction and Analyses: Cellular fatty acids from yeast and plant tissues were extracted according to the method of Peyou-Ndi et al. (2000. *Archives Biochem. Biophys.* 376: 399-408). Samples (100 mg) were treated with 500 μl of 2.5% $H_2SO_4$ in MeOH, sonicated for 20 min, then heated at 80° C. for 90 min. After cooling to room temperature, 750 μl of 0.9% NaCl solution was added, then samples were extracted three times with 500 μl hexane. Hexane extracts were then dried under a stream of nitrogen, reconstituted in a 1:1 mixture of hexane:dichloro-methane to a concentration of 1 mg/100 μl, and analyzed by gas chromatography-mass spectrometry (GC-MS).

Fatty acids were analyzed as methyl ester derivatives on an Agilent 6980GC (Agilent Technologies, Foster City, Calif.) coupled to a JEOL GCMate II mass spectrometer (JEOL USA, Inc., Peabody, Mass.) using an Omegawax 250® (Supelco, St. Louis, Mo.) capillary column, 30 m×0.25 mm×0.25 μm film thickness. The fatty acids were identified by comparison of their retention times and mass spectra with those of authentic standards (Sigma). The inlet (splitless), GC interface, and ion chamber temperatures were 250° C., 250° C., and 230° C., respectively. The volume of sample injected was 1 μl. The GC temperature program for analysis of the hexane extracts, with the exception of the root hair sample, was: initial 110° C. held for 5 min, raised to 160° C. at a rate of 10° C./min, raised to 190° C. at the rate of 1° C./min, raised to 280° C. at the rate of 2° C./min and held at this temp for 2 min. The carrier gas was ultra high purity helium, flow rate 1 ml/min. The root hair hexane extract was analyzed using the following temperature program: initial 80° C. held for 3 min, raised to 170° C. at a rate of 10° C./min, raised to 200° C. at the rate of 1° C./min, raised to 280° C. at the rate of 5° C./min and held at this temperature for 2 min. For further confirmation of double bond positions, methyl esters were converted into their 4,4-dimethyloxaazoline (DMOX) derivatives as previously described (Fay and Richli. 1991. *J. Chromatogr.* 541: 89-98), except that the derivatization reactions were performed at 170° C. for 15 hr. DMOX derivatives were analyzed by GC/MS using the same conditions as described above for the analysis of fatty acid methyl ester derivatives.

Figure 7:
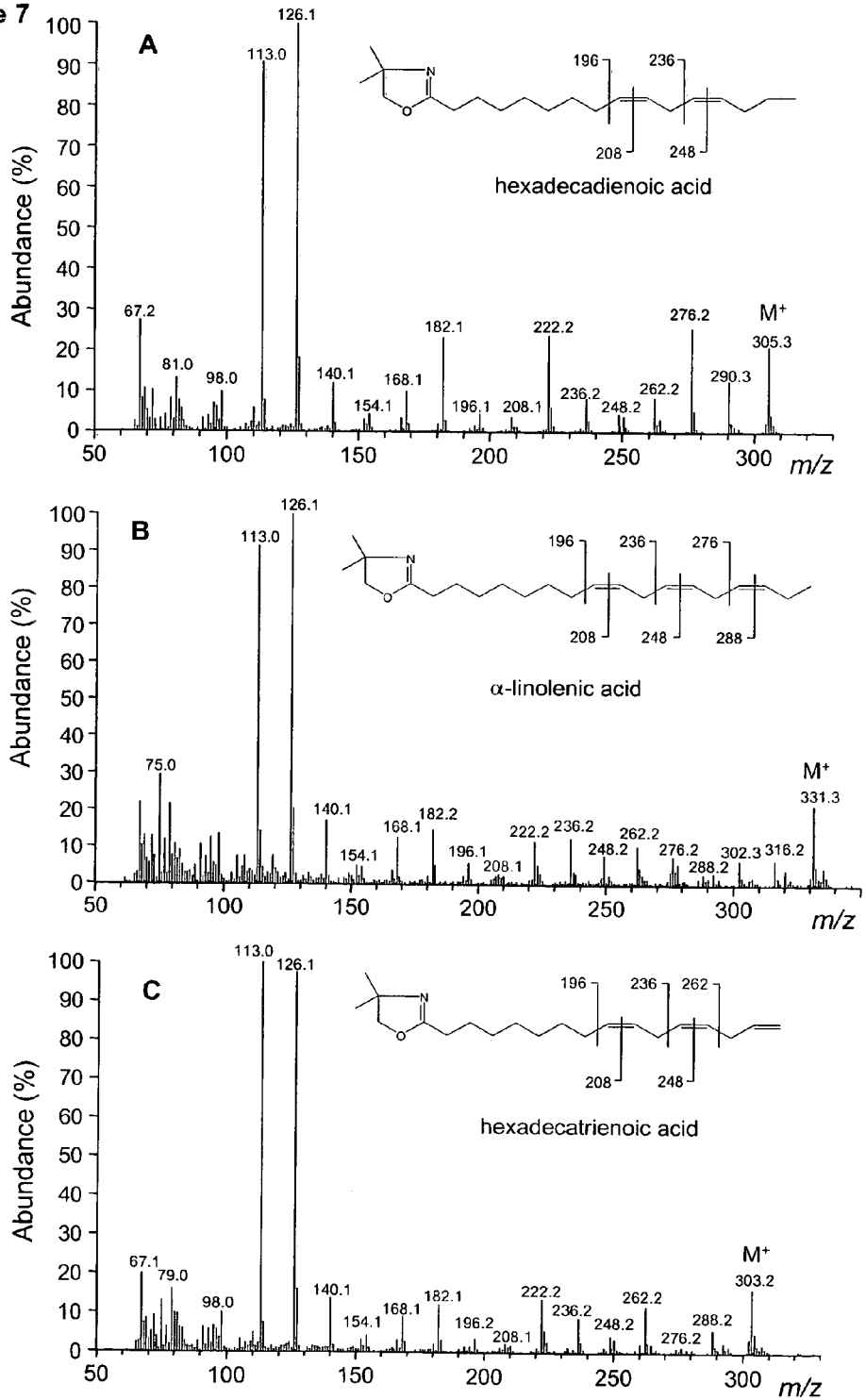
FIGS. 7A-C show the mass spectra of 16.2, 18.3 and 16.3 DMOX derivatives prepared from yeast cells expressing *S. bicolor* desaturases.

As expected, the fatty acid composition of yeast cells transformed with the empty vector (pYES2) alone revealed a simple profile consisting of the four predominant fatty acids (16:0, 16:1 $\Delta^9$, 18:0, and 18:1 $\Delta^9$) typically found in wild type yeast (Stukey et al., 1989. *J. Biol. Chem.* 26: 16537-16544; FIG. 6A—inset). Expression of SbDES1 in yeast cells yielded no additional peaks, regardless of whether or not fatty acids were exogenously provided (not shown). In contrast, expression of SbDES2 resulted in the appearance of one additional peak with a retention time of 27.26 min under all culture conditions, which accounted for approximately 4.4% of the total cellular fatty acids when exogenous fatty acids were not provided (FIG. 6A; Table 1). This peak was identified as 16:2$\Delta^{9, 12}$ by mass spectral analysis (FIG. 6D), suggesting that endogenous palmitoleic acid (16:1$\Delta^9$) served as substrate for SbDES2. The fragmentation pattern of the mass spectrum obtained (FIG. 6D) was identical to one previously published for 16:2 $\Delta^{9, 12}$ (Retrieved from the Internet: <URL: lipidlibrary.co.uk/masspec.html), and was further confirmed by GC/MS analysis of 2,4-dimethyloxazoline (DMOX) derivatives (FIG. 7A). SbDES2 exhibited no detectable $\Delta^{12}$ linoleate desaturase activity, despite the presence of significant endogenous amounts of oleic acid (FIG. 6A—inset). Of particular significance was the observation that the mass spectrum of the 16:2$\Delta^{9, 12}$ fatty acid methyl ester (FIG. 6D) was also identical to that of the 16:2 fatty acid extracted from sorghum root hairs (FIG. 2C).

TABLE 1

Accumulation of fatty acid products in transformed yeast.

| Gene | Products[a] Accumulated | | |
|---|---|---|---|
| | C16:2 | C16:3 | C18:3 |
| SbDES2 | 4.4 (4.2, 4.5) | — | — |
| SbDES3 | — | — | 2.1 (2.3, 1.9) |
| SbDES2/3 | 4.3 ± 3.0 | 1.6 ± 0.2 | — |

[a] Products were identified by GAC/MS as fatty acid methyl ester derivatives. For transgenic yeast harboring pYE2A (SbDES3), exogenous linoleic acid (18:2$\Delta^{9,12}$) was supplemented in the culture medium. Values are expressed as the mean percentage among detectable $C_{12}$-$C_{18}$ fatty acids.

When additional fatty acids were not provided, expression of SbDES3 in yeast yielded no new products. Only strains expressing SbDES3 cultivated in the presence of exogenously supplied linoleic acid (18:2$\Delta^{9, 12}$) produced an additional peak, with a GC retention time of 41.15 min, and accounted for approximately 2.1% of the total cellular fatty acids (FIG. 6B, Table 1). This peak was identified as α-linolenic (18:3$\Delta^{9, 12, 15}$), based on the comparison of the fatty acid methyl ester mass spectrum (FIG. 6E) to that of authentic standards, as well as GC/MS analysis of the corresponding DMOX derivatives (FIG. 7B). Collectively, these results suggest that the preferred substrates for SBDES2 and SBDES3 differed, and were 16:1$\Delta^{9}$ and 18:2$\Delta^{9, 12}$ fatty acids, respectively, under these experimental conditions.

As stated above, SbDES1 exhibited no detectable activity, although it shares 89.7% identity and 92% similarity with SbDES3 at the amino acid level, and was also positioned within the same clade (corresponding to $\Delta^{15}$ desaturases) by phylogenetic analysis (FIG. 5). The reason for this apparent lack of SbDES1 activity in transformed yeast is at present not clear; however, the functionality could potentially by improved through the use of an alternative host system, as previously observed in the case of CvFAD3 from *Chlorella vulgaris* (Suga et al. 2002. *Biosci. Biotechnol. Biochem.* 66: 1314-1327). Initial expression of CvFAD3 in yeast did not yield the expected product linolenic acid in these studies; however, activity was subsequently obtained by expressing the cDNA in transgenic tobacco plants. It was postulated that the lack of activity using the yeast system could potentially be due to translational repression, or alternatively, aberrant targeting to a cellular compartment where the catalytic activity was hindered or the appropriate substrates were unavailable.

Example 7

Production of a 16:3 Fatty Acid Containing a Terminal Double Bond Results from Co-Expression of SbDES2 and SBDES3 in *S. cerevisiae*

To construct additional vectors for co-expression of two ORFs in yeast, the galactose-inducible promoter::SbDES3 (or SbDES1)::terminator expression cassettes were subcloned into the yeast shuttle vector pRS423 containing a his marker (Christianson et al. 1992. Gene 110: 119-122). To achieve this, expression cassettes were amplified from pYE2A and pYE25B using the PCR primers Lgal (5'-gggcgcgccAC GGATTAGAAGCCGCCGAG-3'; SEQ ID NO:13) and Rcyc (5'-gggcgcGCCGCAAATT AAGCCT-TCGA-3'; SEQ ID NO:14), cloned into the pCR®4-TOPO vector (Invitrogen) and confirmed by DNA sequence analyses. The expression cassettes were then excised using BssHII (for SbDES3) or AscI (for SbDES1), gel purified, and subcloned into BssHII- or AscI-digested pRS423, yielding pRS2A (containing SbDES3) and pRS25B (containing SbDES1). These plasmids were then transformed into the yeast strain INVSc1 harboring pYE56D as described above. All yeast transformants were confirmed by colony-PCR, using gene specific primers, and by further restriction analysis performed using isolated plasmid preparations.

As discussed above, expression of SbDES2 in yeast resulted in the production of 16:2$\Delta^{9, 12}$ fatty acid, a proposed precursor to the 16:3 $\Delta^{9, 12, 15}$ starter unit used by polyketide synthases associated with the sorgoleone biosynthetic pathway (Fate and Lynn; Dayan at al., supra). Given the ability of SbDES3 to catalyze the formation of α-linolenic (18:3$\Delta^{9, 12,15}$) from linoleic acid (18:2$\Delta^{9, 12}$), it was postulated that this 16:2 fatty acid would serve as a substrate for SbDES3. Therefore, yeast cells simultaneously expressing both fatty acid desaturases were engineered. Co-expression of SbDES2 and SbDES3 in yeast resulted in the appearance of a new peak with a retention time of 29.4 min (FIG. 6C) and parent ion mass of 264 (FIG. 6F), in addition to the 16:2 peak detected following expression of SbDES2 alone (FIG. 6A). The ion fragments observed in the corresponding mass spectrum were consistent with the fragmentation of a 16:3 fatty acid possessing a terminal double bond (FIG. 6F; compare with FIG. 2D). Moreover, the mass spectrum for the DMOX derivative (FIG. 7C) was identical to recently reported mass spectral data for 16:3 $\Delta^{9, 12,15}$ (Sayanova et al. 2006. *J. Biol Chem.* 281:36533-36541. Similar results were obtained when exogenous palmitic (16:0), palmitoleic (16:1$\Delta^9$), linoleic (18: 2$\Delta^{9, 12}$), α-linolenic (18:3$\Delta^{9, 12,15}$), or γ-linolenic acid (18: 3$\Delta^{6, 9, 12}$) were supplemented to the media, and as expected, a peak corresponding to 18:3$\Delta^{9, 12,15}$ (FIG. 6B, 6E) was also observed in addition to the 16:2 and 16:3 peaks when linoleic acid (18:2$\Delta^{9, 12}$) was provided (data not shown).

To further confirm the identity of the putative 16:3$\Delta^{9, 12, 15}$ fatty acid, the corresponding fatty acid methyl ester was isolated by preparative thin layer chromatography, and nuclear magnetic resonance (NMR) spectroscopy was performed. The 16:3 fatty acid generated by yeast cells over-expressing the SbDES2 and SbDES3 cDNAs was extracted with hexane and isolated by thin layer chromatography using aluminum-backed silica $F_{254}$ plates (10×20 cm$^2$, 0.2 mm silica thickness; EM Science) impregnated with AgNO$_3$. The silica gel plates were pre-treated with a solution of 5% AgNO$_3$ in MeOH—H$_2$O (95:5, v/v), air dried for 60 min, placed in an oven at 80° C. for 16 hours, and allowed to cool to room temperature prior to use. Extracts were then applied to plates and developed using CH$_2$Cl$_2$: ethyl acetate (88:12). The 16:3 fatty acid migrated as a band of R$_f$ 0.12, which was scraped from the plate, extracted with CHCl$_3$, then dried under a stream of nitrogen. An aliquot was analyzed by GC/MS using the same conditions as those described above for the yeast and plant tissue extracts. The 16:3 fatty acid was further characterized by $^1$H-NMR spectroscopy (Bruker DRX 400 UltraShield® spectrometer, XWIN-NMR Software Version 3.1; Bruker, Billerica, Mass.). $^1$H-NMR (CDCl$_3$): δ 5.80 (m, 1H, H-15); 5.30 (m, 4H, H-9, 10, 12, 13); 4.98 (br d, J=17 Hz, 1H, H-16a); 5.02 (br d, J=10 Hz, 1H, H-16b); 4.90-5.01 (br dd, 2H, H-16); 3.71 (s, 3H, OCH$_3$), 2.78 (m, 4H, H-11, 14), 2.32-2.36 (m, 2H, H-2), 2.00 (m, 2H, H-8), 1.49 (m, 2H, H-3), 1.25-1.29 (m, 8H, H-4,5,6,7).

The resulting GC/MS profile of the product isolated by thin layer chromatography was consistent with that of the fatty acid methyl ester peak observed in the initial experiments (FIG. 6C). The $^1$H-NMR chemical shifts of this isolated confirmed the presence of terminal methylene protons (δ 4.98, br d, J=17 Hz, 1H, H-16a; 5.02, br d, J=10 Hz, 1H, H-16b) and the three double bonds (δ 5.80, m, 1H, H-15; δ 5.30, m, 4H, H-9, 10, 12, 13) separated by methylene groups (δ 2.78, m, 4H, H-11, 14) (Chang et al.; Rimando et al., 1998, supra). Importantly, the results of these analyses reveal that sorghum SbDES3 catalyzes the conversion of 16:2 $\Delta^{9, 12}$ fatty acid to the unusual 16:3 Δ9, 12, 15 fatty acid which possesses a terminal double bond.

Example 8

Plant Transformation: SbDES2 and SbDES3 Production in Transgenic *Arabidopsis thaliana*

A two-gene strategy was devised for the production of the unusual 16:3$\Delta^{9, 12, 15}$ fatty acid which possesses a terminal double bond in transgenic plants. Expression of the first gene SbDES2 resulted in the production of 16:2$\Delta^{9, 12}$ fatty acid, the proposed precursor to the 16:3$\Delta^{9, 12, 15}$ fatty acid. Given the ability of SbDES3 to catalyze the formation of α-linolenic (18:3$\Delta^{9, 12, 15}$) from linoleic acid (18:2$\Delta^{9, 12}$), the 16:2 fatty acid can serve as a substrate for SbDES3.

Figure 8:
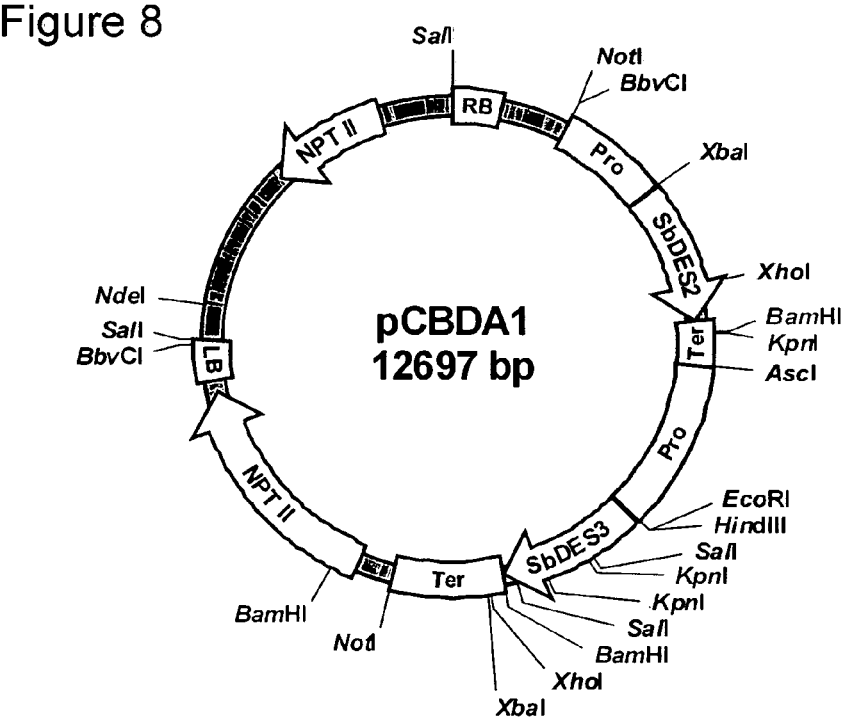
FIG. 8 depicts the plasmid pCBDA1, a binary vector developed to simultaneously express both SbDES2 and SbDES3 in planta. The two expression cassettes are arranged in a head-to-tail orientation.

A binary vector was developed to simultaneously express both SbDES2 and SbDES3 in planta (FIG. 8). For this approach, the complete open reading frame of SbDES2 was positioned downstream of the CaMV 35S promoter, and directly upstream of the polyadenylation region of the *A. tumefaciens* nopaline synthase gene. Similarly, the complete open reading frame for SbDES3 was cloned downstream of the CaMV 35S promoter, and directly upstream of the polyadenylation region of the *A. tumefaciens* octapine synthase gene (FIG. 8). Both transgene cassettes were cloned within the T-DNA borders of a vector derived from pCB302 (Xiang et al. 1999. *Plant Mol. Biol.* 40:711-717). The resulting construct, shown in FIG. 8, contains the two expression cassettes arranged in a head-to-tail orientation and was designated pCBDA1. All DNA manipulations involved in the construction of pCBDA1 involved standard cloning procedures (Sambrook et al., supra).

To generate transgenic plants simultaneously expressing the SbDES2 desaturase and the SbDES3 desaturase enzymes, the plasmid pCBDA1 (FIG. 8) was first transformed into the *Agrobacterium tumefaciens* strain LBA4404 (Hoekma et al. 1983 *Nature* 303:179-180) using the freeze-thaw method devised by An et al. (1988. In: *Plant Molecular Biology Manual*, S. B. Gelvin and R. A. Schilperoort (eds.) Kluwer Academic Publishers, Dordrecht, Pages A3 1-13). As a control, an "empty vector" identical to pCB302, but lacking the inserted SbDES2 and SbDES3 expression cassettes, was also transformed into *A. tumefaciens* strain LBA4404.

The mutant fad7 line of *Arabidopsis thaliana* (L.) Heynh., deficient in hexadecatrienoic acid 16:3 $\Delta^{7, 10, 13}$ (stock number CS3108 available from the *Arabidopsis* Biological Resource Center at Ohio State University), was transformed with the recombinant *A. tumefaciens* strains harboring pCBDA1, or the parent ("empty") vector control using the floral dipping method (Clough and Bent, 1998 *Plant J.* 16:735-743). Seeds from the treated plants were plated on ½×Murashige and Skoog media and transformants were selected and transferred to soil to establish T1 plants. T2 seeds were collected from matured plants and analyzed for fatty acid composition.

To confirm the expression of both the SbDES2 and SbDES3 expression cassettes in the various transgenic *Arabidopsis* lines generated, reverse-transcription PCR (RT-PCR) assays were performed using leaf tissues samples as previously described (Weyman et al., 2006 *Plant Mol. Biol.* 62:547-559). Total RNAs prepared for use in RT-PCR assays were isolated from flash-frozen, pulverized transgenic leaf samples using the Trizol reagent (Invitrogen Corp., Carlsbad, Calif.), with an additional homogenization step of 30 s at 25,000 rpm using a handheld homogenizer. The RNA recovered was then re-purified with a RNeasy Plant Mini-Kit (Qiagen Inc., Valencia, Calif.) per manufacturer's instructions and treated with DNase I. RNA recovery and purity were determined spectrophotometrically, and sample integrity was assessed by agarose gel electrophoresis.

RT-PCR was performed using the SuperScript™ One-Step RT-PCR kit (Invitrogen Corp., Carlsbad, Calif.) according to the manufacturer's instruction. Desaturase gene specific primers ZP38 (5'-ACAACATTTTTACCGCCTTCTCTTCC-3'; SEQ ID NO:15) and ZP35 (5'-AACACGAGAGCGC-GAGGTATTCAACA-3'; SEQ ID NO:16), complementary to the 3'-untranslated region (UTR) of SbDES2 and SbDES3, respectively, were used to synthesize first-strand cDNA. Subsequent PCR reactions were performed using the following gene-specific primer pairs: SbDES2-forward: 5'-GCCTGC-CACTACGACCCCTA-3' (SEQ ID NO:17), reverse: 5'-AG-ATGCACTCCCT GGCTTCG-3' (SEQ ID NO:18); SbDES3-forward: 5'-CCCCTTCCCGCTGCTCTTAT-3' (SEQ ID NO:19), reverse: 5'-AGCACGCCAAGGAGGT-GAAG-3' (SEQ ID NO:20); RT-PCR products were resolved on agarose gel and confirmed by DNA sequence analyses.

To assess whether fatty acid 16:3 $\Delta^{9, 12, 15}$ was produced in plants harboring pCBDA1 (FIG. 8), leaf samples were collected from various transgenic *Arabidopsis* lines, as described above for RT-PCR assays. The leaf fatty acids were extracted according to the method described (Miguel and Browse, 1992 *J. Biol. Chem.* 267:1502-1509), and analyzed by gas chromatography/mass spectrometry (GC-MS) as previously described above.

Figure 9:
FIG. 9 shows the results of both the RT-PCR gene expression assays and fatty acid analyses. Four transgenic lines and 2 empty-vector control lines are shown. A total of 23 independent *Arabidopsis* lines transformed with the pCBDA1 dual-cassette binary vector were screened for the expression of both the SbDES2 and SbDES3 transcripts, as well as for the presence of 16:3 $\Delta^{9, 12, 15}$ fatty acid. Seventeen out of the 23 lines were found to express the transgenes; both the SbDES2 and SbDES3 transcripts were detected in all 17 of these positive lines.

The results of both the RT-PCR gene expression assays and fatty acid analyses are shown in FIG. 9. A total of 23 independent *Arabidopsis* lines transformed with the pCBDA1 dual-cassette binary vector were screened for the expression of both the SbDES2 and SbDES3 transcripts, as well as for the presence of 16:3 $\Delta^{9, 12, 15}$ fatty acid. Seventeen out of the 23 lines were found to express the transgenes; both the SbDES2 and SbDES3 transcripts were detected in all 17 of these positive lines.

Figure 10:
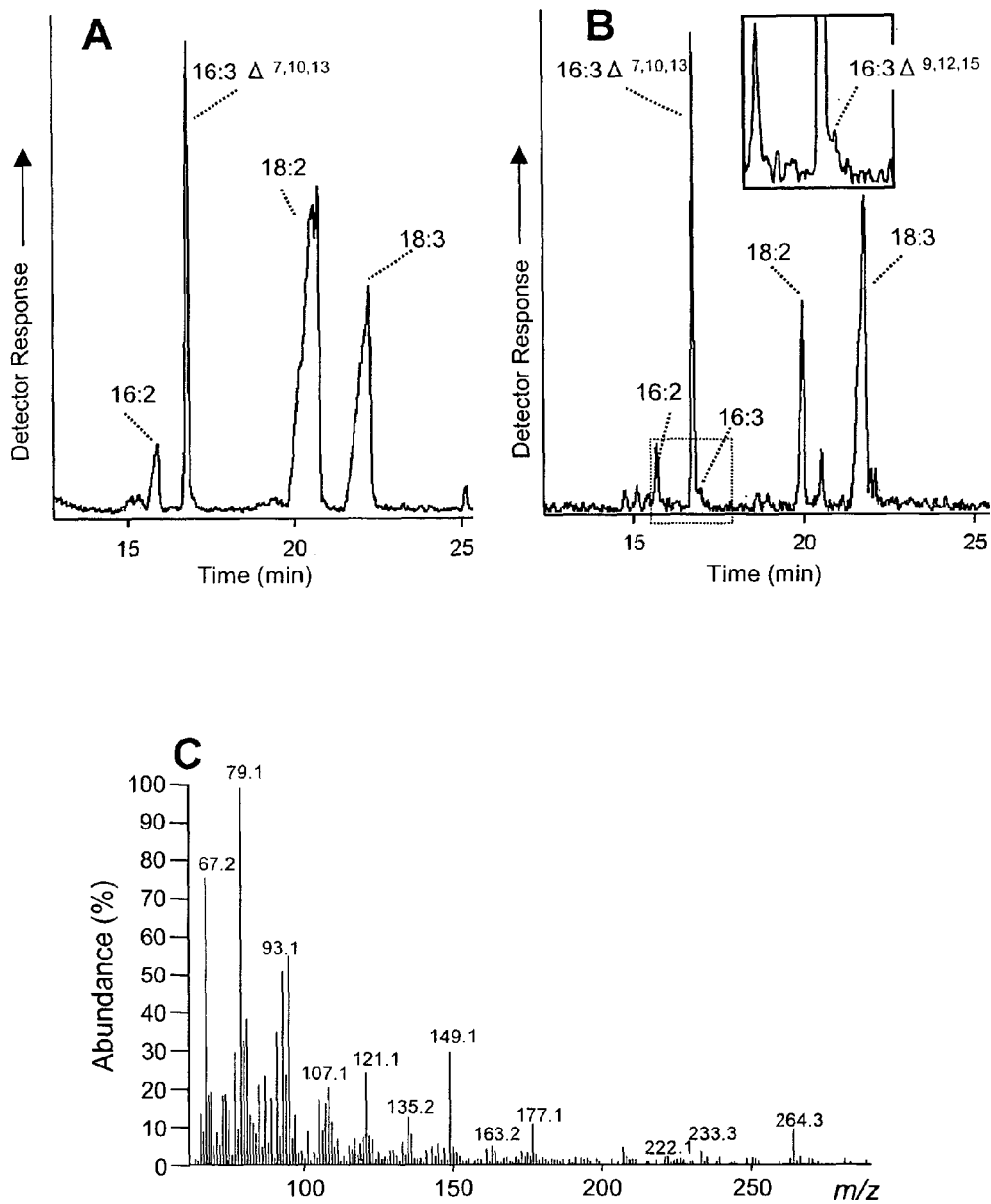
FIGS. 10A-C depict fatty acid profiles from transgenic lines. A distinct peak was observed in transgenic lines expressing SbDES2 and SbDES3 (FIG. 10B), in contrast to an empty vector control (FIG. 10A). The mass spectrum of this peak shows the characteristic ion fragments for this fatty acid, m/z 264, 233 and 222 (FIG. 10C), which confirmed the identity of the fatty acid processing terminal double bond.

Importantly, significant accumulation of fatty acid 16:3 $\Delta^{9, 12, 15}$ was detected in selected lines pCBDA1-16, 17, 18, and 19. A distinct peak was observed in transgenic lines expressing SbDES2 and SbDES3 (FIG. 10B), in contrast to an empty vector control (FIG. 10A). The mass spectrum of this peak shows the characteristic ion fragments for this fatty acid, m/z 264, 233 and 222 (FIG. 10C), which confirmed the identity of the fatty acid processing terminal double bond.

These experiments demonstrate the utility of the invention described herein: transgenic plants expressing both SbDES2 and SbDES3 desaturase enzymes accumulate 16:3 $\Delta^{9, 12, 15}$ which possesses a terminal double bond. The ability of SbDES2 and SbDES3 to act consecutively to convert 16:1 fatty acids to 16:3 fatty acids having a terminal double bond in planta is a central feature of this technology.

The present proof-of-concept can be further optimized for the production of fatty acids with a terminal double bond at higher levels or in specific tissues, for example, by the use of alternative promoter elements or other genetic elements required for the optimal expression of the transgene cassettes employed.

SbDES2 and SbDES3 represent a novel subclass of plant-specific desaturase enzymes, exhibiting a substrate profile that has not previously been demonstrated for any plant to our knowledge. Moreover, phylogenetic analyses of putative and functionally characterized plant-specific desaturase enzymes indicates that SbDES2 and SbDES3 fall within a distinct clade of desaturases.

All publications and patents mentioned in this specification are herein incorporated by reference to the same extent as if each individual publication or patent was specifically and individually indicated to be incorporated by reference.

The foregoing description and certain representative embodiments and details of the invention have been presented for purposes of illustration and description of the invention. It is not intended to be exhaustive or to limit the invention to the precise forms disclosed. It will be apparent to practitioners skilled in this art that modifications and variations may be made therein without departing from the scope of the invention.

We claim:

1. A DNA construct comprising a nucleotide sequence operably linked to a promoter that drives expression in a plant cell, wherein said nucleotide sequence is an isolated nucleic acid molecule comprising the nucleotide sequence set forth in SEQ ID NO: 3, wherein the nucleic acid molecule encodes a $\Delta^{15}$ fatty acid desaturase molecule capable of catalyzing the formation of a terminal double bond on a fatty acid molecule, converting a $16:3\Delta^{9,12}$ fatty acid substrate to its $16:3\Delta^{9,12,15}$ trienoic form.

2. A method of manipulating content of $16:3\Delta^{9,12,15}$ in a plant or plant cell, comprising introducing into a plant at least one DNA construct comprising a nucleotide sequence operable linked to a promoter that drives expression in a plant cell, wherein said nucleotide sequence is an isolated nucleic acid molecule comprising the nucleotide sequence set forth in SEQ ID NO:3, wherein the nucleic acid molecule encodes a desaturase having an activity of catalyzing the formation of a terminal double bond in a fatty acyl chain, converting a 16:3 $\Delta^{9,12}$ fatty acyl substrate to its $16:3\Delta^{9,12,15}$ trienoic form.

3. A host cell having stably incorporated into its genome at least one DNA construct of claim 1.

4. A method of producing $16:3\Delta^{9,12,15}$, an unsaturated fatty acid having a terminal double bond, comprising transfecting or transforming a cell with the isolated nucleic acid molecule of claim 1 and culturing or cultivating the cell under conditions such that said unsaturated fatty acid is produced.

5. A method of producing a cell capable of generating $16:3\Delta^{9,12,15}$, comprising introducing into said cell the nucleic acid molecule of claim 1, wherein the nucleic acid molecule encodes a desaturase having an activity of catalyzing the formation of a terminal double bond in a fatty acyl chain, converting a $16:3\Delta^{9,12}$ fatty acyl substrate to its $16:3\Delta^{9,12,15}$ trienoic form.

6. The method of claim 5, wherein the cell is selected from the group consisting of a plant cell and a microbial cell.

7. The method of claim 6, wherein the plant cell is a cell from an oilseed plant.

8. The method of claim 7, wherein the oilseed crop is selected from the group consisting of flax (*Linum* sp.), rapeseed (*Brassica* sp.), soybean (*Glycine* and *Sola* sp.), sunflower (*Helianthus* sp.), cotton (*Gossypium* sp.), corn (*Zea mays*), olive (*Olea* sp.), safflower (*Carthamus* sp.), cocoa (*Theobroma caeca*), and peanut (*Arachis* sp.).

9. A transgenic plant containing the nucleic acid sequence according to claim 1 or a progeny of said plant containing the nucleic acid sequence according to claim 1 wherein the level of accumulation of a $16:3\Delta^{9,12,15}$ fatty acid desaturase molecule capable of catalyzing the formation of a terminal double bond in a fatty acyl chain, converting a $16:3\Delta^{9,12}$ fatty acyl substrate to its $16:3\Delta^{9,12,15}$ trienoic form in said plant or progeny of said plant is altered when compared to plants of the same species which have not been transformed.

10. The transgenic plant of claim 9 wherein the level of $16:3\Delta^{9,12,15}$ is altered when compared to plants of the same species which have not been transformed.

11. The method of claim 2, wherein the plant cell is a cell from an oilseed plant.

12. The method of claim 11, wherein the oilseed crop is selected from the group consisting of flax (*Linum* sp.), rapeseed (*Brassica* sp.), soybean (*Glycine* and *Sola* sp.), sunflower (*Helianthus* sp.), cotton (*Gossypium* sp.), corn (*Zea mays*), olive (*Olea* sp.), safflower (*Carthamus* sp.), cocoa (*Theobroma cacca*), and peanut (*Arachis* sp.).

13. The method of claim 2, further comprising the step of recovering the unsaturated $16:3\Delta^{9,12,15}$.

14. An isolated recombinant nucleic acid molecule consisting of the nucleotide sequence set forth in SEQ ID NO: 3.

15. A DNA construct comprising a nucleotide sequence operably linked to a promoter that drives expression in a plant cell, wherein said nucleotide sequence is an isolated recombinant nucleic acid molecule comprising the nucleotide sequence set forth in SEQ ID NO: 3.

16. A vector comprising the DNA construct of claim 15.

17. A host cell having stably incorporated into its genome at least one DNA construct of claim 15.

18. A method of producing an unsaturated fatty acid having a terminal double bond comprising transfecting or transforming a cell with the isolated nucleic acid molecule of claim 15 and culturing or cultivating the cell under conditions such that said unsaturated fatty acid is produced.

19. A method of producing a cell capable of generating $16:3\Delta^{9,12,15}$ comprising, introducing into said cell the nucleic acid molecule of claim 15, wherein the nucleic acid molecule encodes a desaturase having an activity of catalyzing the formation of a terminal double bond in a fatty acyl chain, converting a $16:3\Delta^{9,12}$ fatty acyl substrate to its $16:3\Delta^{9,12,15}$ trienoic form.

20. The method of claim 19, wherein the cell is selected from the group consisting of a plant cell and a microbial cell.

21. The method of claim 20, wherein the plant cell is a cell from an oilseed plant.

22. The method of claim 21, wherein the oilseed crop is selected from the group consisting of flax (*Linum* sp.), rapeseed (*Brassica* sp.), soybean (*Glycine* and *Sola* sp.), sunflower (*Helianthus* sp.), cotton (*Gossypium* sp.), corn (*Zea mays*), olive (*Olea* sp.), safflower (*Carthamus* sp.), cocoa (*Theobroma cacca*), and peanut (*Arachis* sp.).

23. A transgenic plant containing the nucleic acid sequence according to claim 15 or a progeny of said plant containing the nucleic acid sequence according to claim 15 wherein the level of accumulation of a $16:3\Delta^{9,12,15}$ fatty acid desaturase molecule capable of catalyzing the formation of a terminal double bond in a fatty acid chain, converting a $16:3\Delta^{9,12}$ fatty acyl substrate to its $16:3\Delta^{9,12,15}$ trienoic form in said plant or progeny of said plant is altered when compared to plants of the same species which have not been transformed.

24. The transgenic plant of claim 23 wherein the level of $16:3\Delta^{9,12,15}$ is altered when compared to plants of the same species which have not been transformed.

25. A method of manipulating content of $16:3\Delta^{9,12,15}$ in a plant or plant cell comprising introducing into a plant at least one DNA construct comprising a nucleotide sequence operably linked to a promoter that drives expression in a plant cell, wherein said nucleotide sequence is an isolated nucleic acid molecule comprising the nucleotide sequence set forth in SEQ ID NO: 3 and then expressing said nucleic acid sequence in said plant or plant cell so as to thereby increase the accumulation of $16:3\ \Delta^{9,\ 12,\ 15}$ in the plant or plant cell.

26. The method of claim 25, wherein the plant is selected from an oilseed crop.

27. The method of claim 26, wherein the oilseed crop is selected from the group consisting of flax (*Linum* sp.), rapeseed (*Brassica* sp.), soybean (*Glycine* and *Sola* sp.), sunflower (*Helianthus* sp.), cotton (*Gossypium* sp.), corn (*Zea mays*), olive (*Olea* sp.), safflower (*Carthamus* sp.), cocoa (*Theobroma cacca*), and peanut (*Arachis* sp.).

28. The method of claim 25, further comprising the step of recovering the unsaturated fatty acid.

29. A transgenic plant containing the nucleic acid sequence according to claim 15 or a progeny of said plant containing the nucleic acid sequence according to claim 15 wherein the level of accumulation of a $16:3\Delta^{9,12,15}$ fatty acid desaturase molecule capable of catalyzing the formation of a terminal double bond in a fatty acid chain, converting a $16:3\Delta^{9,12,15}$ fatty acyl substrate to its $16:3\Delta^{9,12,15}$ trienoic form in said plant or progeny of said plant is altered when compared to plants of the same species which have not been transformed.

30. The transgenic plant of claim 29 wherein the level of $16:3\Delta^{9,12,15}$ is altered when compared to plants of the same species which have not been transformed.

\* \* \* \* \*